(12) United States Patent
Epp et al.

(10) Patent No.: US 11,419,893 B2
(45) Date of Patent: Aug. 23, 2022

(54) METHOD OF PRODUCING A DESIGNER BLOOD PRODUCT, METHOD OF USING A DESIGNER BLOOD PRODUCT, AND DIET FOR SELECTIVELY ENHANCING BLOOD PROFILE

(71) Applicant: CENTRAL BIOMEDIA, INC., Lenexa, KS (US)

(72) Inventors: Tammi Sue Epp, Ottumwa, IA (US); Jeffery Scott Pendergraft, Alpine, TX (US); Donald E. Myers, Olathe, KS (US); William G. Skelly, Overland Park, KS (US); Nicole Green, Kansas City, MO (US)

(73) Assignee: CENTRAL BIOMEDIA, INC., Lenexa, KS (US)

( * ) Notice: Subject to any disclaimer, the term of this patent is extended or adjusted under 35 U.S.C. 154(b) by 213 days.

(21) Appl. No.: 16/902,560

(22) Filed: Jun. 16, 2020

(65) Prior Publication Data

US 2020/0306298 A1   Oct. 1, 2020

Related U.S. Application Data

(62) Division of application No. 14/555,105, filed on Nov. 26, 2014, now Pat. No. 10,688,129.

(60) Provisional application No. 61/909,004, filed on Nov. 26, 2013.

(51) Int. Cl.
| | |
|---|---|
| *A61K 35/16* | (2015.01) |
| *A61K 39/09* | (2006.01) |
| *A61K 39/02* | (2006.01) |
| *A61K 39/108* | (2006.01) |
| *A61K 39/12* | (2006.01) |
| *A61K 39/00* | (2006.01) |
| *A61K 39/08* | (2006.01) |
| *C07K 16/00* | (2006.01) |
| *A61M 1/00* | (2006.01) |

(52) U.S. Cl.
CPC .......... *A61K 35/16* (2013.01); *A61K 39/0002* (2013.01); *A61K 39/0208* (2013.01); *A61K 39/0258* (2013.01); *A61K 39/08* (2013.01); *A61K 39/092* (2013.01); *A61K 39/12* (2013.01); *A61M 1/00* (2013.01); *A61K 2039/545* (2013.01); *A61K 2039/552* (2013.01); *A61K 2039/70* (2013.01); *C07K 16/00* (2013.01); *C12N 2710/16034* (2013.01); *C12N 2760/16134* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 3,992,521 | A | 11/1976 | Le Minor |
| 4,659,563 | A | 4/1987 | Dobkin |
| 4,732,752 | A | 3/1988 | Stephan |
| 5,230,902 | A | 7/1993 | Gold et al. |
| 5,548,066 | A | 8/1996 | Leneau et al. |
| 5,681,565 | A | 10/1997 | Gristina et al. |
| 5,772,999 | A | 6/1998 | Greenblatt et al. |
| 5,817,312 | A | 10/1998 | Gristina et al. |
| 6,310,090 | B1 | 10/2001 | Hayek |
| 6,339,068 | B1 | 1/2002 | Krieg et al. |
| 6,569,447 | B2 | 5/2003 | Kisic et al. |
| 6,770,278 | B1 | 8/2004 | Skelly |
| 7,045,131 | B2 | 5/2006 | Patti et al. |
| 8,354,249 | B2 | 1/2013 | Nur et al. |
| 2002/0015745 | A1 | 2/2002 | Hayek et al. |
| 2002/0122803 | A1 | 9/2002 | Kisic et al. |
| 2002/0159997 | A1 | 10/2002 | Patti et al. |
| 2005/0287146 | A1 | 12/2005 | Patti et al. |
| 2007/0037170 | A1 | 2/2007 | Nur et al. |
| 2011/0135581 | A1 | 6/2011 | Weaver et al. |
| 2011/0274789 | A1 | 11/2011 | Mikelsaar et al. |
| 2012/0087988 | A1 | 4/2012 | Gold |
| 2012/0093936 | A1 | 4/2012 | Lindenberg et al. |
| 2012/0183521 | A1 | 7/2012 | Sinatra et al. |

FOREIGN PATENT DOCUMENTS

| | | |
|---|---|---|
| CN | 102584993 A | 7/2012 |
| CN | 103651804 A | 3/2014 |
| EP | 2 303 291 B1 | 2/2013 |
| JP | 61 100522 | 5/1986 |

(Continued)

OTHER PUBLICATIONS

Warren, Lori K.; "Potential Immuni-stimulatory Nutrients for the Equine Athlete", *4th European Equine Nutrition & Health Congress*; Apr. 18-19, 2008; pp. 28-45; The Netherlands.
Vereenooghe, et al.; "*Evaluation of the effect of RGT treatment on airways in racehorses*"; pamphlet received from The Dorothy Havemeyer Foundation IAD Workshop, "Inflammatory Airway Disease; one syndrome, multiple pathways" in Cabourg, Normandy, France; Oct. 13-14, 2014 (12 pages).
International Search Report and Written Opinion dated Feb. 4, 2015 for corresponding PCT application, PCT/US2014/067718, international filing date, Nov. 26, 2014.

(Continued)

*Primary Examiner* — Nora M Rooney
(74) *Attorney, Agent, or Firm* — Stinson LLP

(57) ABSTRACT

A method for treating and/or mitigating a respiratory condition in an equine patient. The method comprises administering a blood product to the equine patient via localized delivery to the lungs. The blood product is produced by pre-treating at least one donor horse with a diet and immunization regime for at least one month before collecting the blood from the donor horse and processing it to make the blood product. The pre-treatment diet comprises feeding the donor horse a combined amount of EPA and DHA of at least 4.25 mg/kg horse/day with the EPA:DHA ratio ranging from 1:5-5:1 and alfalfa hay. The immunization regimen comprises immunizing the donor horse with *Rhodooccus equi*.

18 Claims, No Drawings

(56) References Cited

FOREIGN PATENT DOCUMENTS

| | | |
|---|---|---|
| RU | 2 091 072 C1 | 9/1997 |
| RU | 2 413 533 C2 | 5/2009 |
| RU | 2 494 760 C1 | 4/2012 |
| UA | 19 309 U | 12/2006 |
| WO | WO 1996/016985 | 6/1996 |
| WO | WO 2003/026682 A1 | 4/2003 |
| WO | WO 2004/033665 A2 | 4/2004 |
| WO | WO 2005/077299 | 8/2005 |
| WO | WO 2011/029903 A1 | 3/2011 |
| WO | WO 2014/072468 A1 | 5/2014 |
| WO | WO 2014/108497 A2 | 7/2014 |

OTHER PUBLICATIONS

Carlson, Eric R. et al.; "Effects of serum and autologous conditioned serum on equine articular chondrocytes treated with interleukin-1β"; AJVR, Vo. 74, No. 5, May 2013; pp. 700-705.

Steffanus, Denise; "Platelet-Rich Plasma Treatment for Bleeders Called Junk Science"; Aug. 23, 2012; pp. 1-10.

Hall, Jean A. et al.; "Dietary (n-3) Fatty Acids from Menhaden Fish Oil Alter Plasma Fatty Acids and Leukotriene B Synthesis in Healthy Horses"; J. Vet. Intern. Med.; 2004; vol. 18; pp. 871-879.

Ainsworth, Dorothy M. et al.; "IgG antibody responses to an inhaled antigen in horses with "heaves" (recurrent airway obstruction); Veterinary Immunology and Immunopathology"; 2002; vol. 84; pp. 169-180.

Richard. E. A. et al.; "Serum concentration of surfactant protein D in horses with lower airway inflammation": Equine Veterinary Journal; 2012; vol. 44; pp. 277-281.

Tabas, Ira et al.; "Anti-Inflammatory Therapy in Chronic Disease: Challenges and Opportunities"; Science; Jan. 11, 2013; vol. 339; pp. 166-172.

Murdoch, Jenna R. et al.; "Chronic inflammation and asthma"; Mutation Research; 2010; vol. 690; pp. 24-39.

Batard, T. et al.; "Anti-inflammatory activity of sublingual immunoglobulin (SLIG) in a murine model of allergen-driven airway inflammation": Vaccine; 2012; vol. 30; pp. 5666-5674.

"Immune Deficiency due to IgG subclass"; http:www.cipusa.org/IgG3deficiency.html; Apr. 3, 2013.

Hooper-McGrevy, Kathleen E. et al.; "Immunoglobulin G Subisotype Responses of Pneumonic and Healthy, Exposed Foals and Adult Horses to Rhodococcus equi Virulence-Associated Proteins": American Society for Microbiology; May 2013; pp. 345-351.

Mejías, Asunción, et al.; "Anti-Respiratory Syncytial Virus (RSV) Neutralizing Antibody Decreases Lung Inflammation, Airway Obstruction, and Airway Hyperresponsiveness in a Murine RSV Model": American Society for Microbiology; May 2004; pp. 1811-1822.

Atochina, Elena N. et al.; "Attenuated allergic airway hyperresponsiveness in C57BL/6 mice is associated with enhanced surfactant protein (SP)-D production following allergic sensitization"; Respiratory Research; Dec. 8, 2003; pp. 1-12.

Katavolos, P. et al.; "Clara Cell Secretory Protein is Reduced in Equine Recurrent Airway Obstruction"; Veterinary Pathology Online; vol. 46; 2009; pp. 604-613.

Fortier, Guillaume et al.; "Herpesviruses in respiratory liquids of horses: Putative implication in airway inflammation and association with cytological features"; Veterinary Microbiology; vol. 139; 2009; pp. 34-41.

Wood, J. L. N. et al.; "Association between Respiratory Disease and Bacterial and Viral Infections in British Racehorses"; Journal of Clinical Microbiology; Jan. 2005; vol. 43, No. 1; pp. 120-126.

Hamm, D. et al.; "Caprine serum fraction immunomodulator as supplemental treatment of lower respiratory disease in the horse": Equine Vet. J.; vol. 34; 2002; pp. 71-75.

Epp, Tammi S. et al.; "The Effectiveness of Immunotherapy in Treating Exercise-Induced Pulmonary Hemorrhage"; Journal of Equine Veterinary Science; vol. 29, No. 6; 2009; pp. 527-532.

Sehra, Sarita et al.; "Airway IgG Counteracts Specific and Bystander Allergen-Triggered Pulmonary Inflammation by a Mechanism Dependent on Fc γR and IFN-γ"; J Immunol; vol. 171; 2003; pp. 2080-2089.

Couëtil, Laurent L. et al.; "Inflammatory Airway Disease of Horses": J Vet Intern Med; vol. 21; 2007; pp. 356-361.

Ishikawa, Yumiko et al.; "Antigen-Specific IgG ameliorates allergic airway inflammation via Fcγ receptor IIB on dendritic cells"; Respiratory Research; 2011; vol. 12:42; pp. 1-10.

Hodgson, J. L. et al.; "Inflammatory Airway Disease": International Veterinary Information Services; Aug. 16, 2002; pp. 1-32.

Ragland, W. L. et al.; "Passive Immunotherapy of Equine Respiratory Disease: Treatment of Acutely Ill Horses with Equine Immunoglobulin": The Equine Athlete; vol. 8, No. 6, Nov./Dec. 1995; pp. 1-7.

Christmann U. et al.; "Abnormalities in lung surfactant in horses clinically affected with recurrent airway obstruction (RAO) "; J. Vet Intern Med.; Nov.-Dec. 2008; PubMed—NCBI; p. 1.

Katavolos P. et al.; "Clara cell secretory protein increases phagocytic and decreases oxidative activity of neutrophils"; Vet Immunol Immunopathol.; 2011; PubMed—NCBI; p. 1.

Nakata K. et al.; "The transfer of maternal antigen-specific IgG regulates the development of allergic airway inflammation early in life in an FcRn-dependent manner"; Biochem Biophys Res Commun.; 2010; PubMed—NCBI; p. 1.

Balzar, S. et al.; "Subtle Immunodeficiency in severe asthma: IgA and IgG2 correlate with lung function and symptoms"; Int Arch Allergy Immunol.; 2006; PubMed—NCBI; p. 1.

Khol-Parisini A. et al.; "Effects of feeding sunflower oil or seal blubber oil to horses with recurrent airway obstruction"; Can J Vet Res.; 2007; PubMed—NCBI; p. 1.

Hall, J. A. et al.; "Effect of type of dietary polyunsaturated fatty acid supplement (corn oil or fish oil) on immune responses in healthy horses"; J Vet Intern Med.; Nov.-Dec. 2004; PubMed—NCBI; p. 1.

Klaus Termeyer, W. B. et al.; "Quantitative Immunoglobulins and IgG subclasses in patents with corticosteroid-dependent reversible airway obstruction"; Arm Allergy; 1989; PubMed—NCBI; p. 1.

Rogerio, A. P. et al.; "Resolvin D1 and aspirin-triggered resolving D1 promote resolution of allergic airways responses"; J Immunol.; 2012; PubMed—NCBI; p. 1.

Zemann, B. et al.; "Oral administration of specific antigens to allergy-prone infant dogs induces IL-10 and TGF-beta expression and prevents allergy in adult life"; J Allergy Clin Immunol.; 2003; PubMed—NCBI; p. 1.

Carlsen K. H. et al.; "Acute bronchiolitis in infancy. The relationship to later recurrent obstructive airways disease": Eur J Respir Dis.; 1987; PubMed—NCBI; p. 1.

Pirie, R. S. et al.; "Inhaled endotoxin and organic dust particulates have synergistic proinflammatory effects in equine heaves (organic dust-induced asthma)"; Clin Exp Allergy.; 2003; PubMed—NCBI; p. 1.

Kirschvink, N.; et al.; "Effect of nutritional antioxidant supplementation on systemic and pulmonary antioxidant status, airway inflammation and lung function in heaves-affected horses": Equine Vet J.; 2002; PubMed—NCBI; p. 1.

Miller, T. L. et al.; "Recombinant human Clara cell secretory protein in acute lung injury of the rabbit; effect of route of administration"; Pediatr Crit Care Med.; 2005; PubMed—NCBI; p. 1.

Pirie, R. S. et al.; "Endotoxin contamination contributes to the pulmonary inflammatory and functional response to Aspergillus fumigatus extract inhalation in heaves horses": Clin Exp Allergy.; 2003; PubMed—NCBI; p. 1.

Beeler-Marfisi J. et al.; "Experimental induction of recurrent airway obstruction with inhaled fungal spores, lipopolysaccharide, and silica microsperes in horses"; Am J Vet Res.; 2010; PubMed—NCBI; p. 1.

Dunkel, B. et al.; "Stimulus-dependent release of tissue-regenerating factors by equine platelets"; Equine Veterinary Journal; vol. 44; 2012; pp. 346-354.

Hildreth Tammi Sue, et al.; "Is immunotherapy in reducing exercise-induced pulmonary haemorrhage"; 2003; The FASEB J. 17, p. A939.

(56) References Cited

OTHER PUBLICATIONS

Steffanus, Denise; "*Thoroughbred Times*"; http://www.thoroughbredtimes.com/news/print.aspx; Nov. 9, 2012.
Davis, Jonathan et al.; "*Oral Administration of Concentrated Equine Serum to Newborn Foals Prevents Failure of Passive Transfer of Immunoglobulin and Provides Passive Immunity for Rhodococcus equi*"; General Equine Medicine; vol. 41; 1995; pp. 176-177.
Gröndahl, Gittan et al.; "*Opsonic effect of equine plasma from different donors*"; Veterinary Microbiology; vol. 56; 1997; pp. 227-235.
Couetil et al., "*Inflammatory Airway Disease of Horses-Revised Consensus Statement*", ACVIM Consensus Statement J Vet Intern Med 30:503-515, 2016.
Kurucz, et al, "*Current Animal Models of Bronchial Asthma*", Curr. Pharm. Des. 12:3174-3194, 2006.
Mukherjee et al., "*Allergic Asthma: Influence of Genetic and Environmental Factors*", J. Biol. Chem. 286(38):32883-32889, 2011.

METHOD OF PRODUCING A DESIGNER BLOOD PRODUCT, METHOD OF USING A DESIGNER BLOOD PRODUCT, AND DIET FOR SELECTIVELY ENHANCING BLOOD PROFILE

CROSS-REFERENCE TO RELATED APPLICATIONS

This application claims priority to and is a Divisional of U.S. patent application Ser. No. 14/555,105, filed on Nov. 26, 2014 which claims priority to U.S. Provisional Application Ser. No. 61/909,004, filed on Nov. 26, 2013, each of which is incorporated herein by reference in its entirety.

STATEMENT REGARDING FEDERALLY SPONSORED RESEARCH OR DEVELOPMENT

Not applicable.

BACKGROUND OF THE INVENTION

Field of the Invention

The present invention is generally directed to a method of making a designer blood product having an enhanced profile comprising preferred or helpful components for preventing or mitigating a specific condition or disease in relatively high concentration and/or having undesirable or harmful components for preventing or mitigating a specific condition or disease in relatively low concentration. The designer blood product is administered to patient animals to prevent or mitigate a specific condition or disease. In a preferred embodiment, the blood product is a serum with an enhanced profile of components that assist or support the patient animal's immune system in resolving an inappropriate immune response resulting in chronic, exuberant, or non-resolving inflammation.

Description of the Related Art

Inflammation is a natural immune response to harmful stimuli. It involves the recruitment of immunological cells and the release of factors that assist in fighting infections, ridding the body of harmful stimuli, and promoting healing. However, inflammation itself can impair healthy cell, tissue, and body functions if it is prolonged or becomes chronic. The organization of the immune system is highly complex with considerable redundancy and compensatory networking pathways that are tightly regulated. In non-resolving chronic inflammatory diseases, there is a deficiency in the regulation of anti-inflammatory pathways that prevent the resolution of exuberant inflammation. Therapeutic targeting of specific components and pathways or eliminating protective and necessary inflammatory pathways has not been successful due to the complex and redundant nature of the immune system.

Many inflammatory conditions and diseases affect livestock and other domesticated or companion animals. Examples include laminitis, osteoarthritis, exertional rhabdomyolysis (also known as tying-up), myositis, colic (including colitis and right dorsal colitis, enteritis, endotoxemia, pre- and post-surgical occurrences, impaction, gas, gastric ulcers, torsions, and volvulus), ophthalmic conditions (including uveitis and refractory corneal ulcers), endometritis, inflammation or tears in tendons, ligaments, and associated structures (i.e. sheaths), developmental orthopedic diseases (such as Osteochondritis Dessicans (OCD), lesions, and cysts), chronic wounds, neurologic conditions (such as Equine Protozoal Myelitis (EPM), encephalitis, and West Nile Virus (WNV)), dermatitis, autoimmune conditions, and oxidative and inflammatory stress associated with severe exercise and competition (such as 3-day eventing, endurance, transportation, and racing). Inflammation is also associated with certain respiratory conditions and diseases such as Exercise-Induced Pulmonary Hemorrhage (EIPH), Inflammatory Airway Disease (IAD), and Recurrent Airway Obstruction (RAO)/Chronic Obstructive Pulmonary Disease (COPD) commonly experienced in horses, particularly race horses and other performance horses. Second only to musculoskeletal disease, respiratory diseases (including EIPH and IAD) are the most common causes of poor performance, interruption and loss of training time, veterinary expenses, and forced retirement in performance horses. Recurrent Airway Obstruction (RAO) or Chronic Obstructive Pulmonary Disease (COPD), also known as heaves, is also extremely common.

By way of a specific example, IAD is non-infectious airway inflammation diagnosed by increased total nucleated cell counts in one of three types of categories (mixed, eosinophilic, or mast cell) upon cytologic examination of bronchoalveolar lavage fluid (BALF) and evidence of pulmonary dysfunction (such as lower airway obstruction, airway hyper-responsiveness, or impaired blood gas exchange at rest or during exercise). Horses with IAD exhibit poor performance, exercise intolerance, or coughing (with or without excess tracheal mucus). An episode of IAD may last several weeks, months, or years. IAD and RAO are now thought as a continuum of the same disease process, and it is currently unknown which horses may progress from IAD to RAO. The incidence rate tends to decline with age in racehorses, which suggests some level of acquired immunity. However, increases in incidence and severity, as well as progression are commonly seen in older, stabled performance horses.

Complex aberrant innate and adaptive immune responses are involved in the pathogenesis of these multifactorial diseases. IAD is caused by a number of factors that together initiate, accentuate, and perpetuate inflammation of the airways. These factors include exposure to aerosolized particles (such as Beta-D-Glucan in molds, fungi, or pollens), dust (including hay, grain, stable bedding, mite debris/feces, vegetative material/plant debris), noxious gases (such as ammonia, hydrogen sulfide, sulfur dioxide, nitrogen dioxide, and carbon monoxide), inhaled environmental pollutants (such as ozone, metallic or carbon particles, and bacterial endotoxin), and bacterial and viral pathogens (such as *Actinobacillus, Streptococcus zooepidemicus, Streptococcus pneumoniae, Pasteurellaceae, Bordatella bronchiseptica, Fusobacterium, Mycoplasma*, equine influenza, equine herpes virus 1 and 4, and equine rhinitis A and B). Exposure to these factors may result from co-mingling, stabling, dust from arena activities, barn cleaning, feeding, accumulation of waste excretions (ammonia, for example), or poor ventilation. The effect of these factors may be compounded by: cold and dry air, which injures airway mucosa; strenuous or high-intensity exercise training and racing, which impairs pulmonary defenses; transport over long distances, which reduces pulmonary macrophage function and encourages deep inhalation of dust; and/or the genetic make-up of the animal, which dictates the level to which the animal may be predisposed to responding to these factors in an unhealthy way.

Current treatments for chronic lung inflammation include quintessential environmental intervention and the use of corticosteroids in combination with bronchodilators, which serve to reduce exposure to inducing allergens and provide symptomatic relief without directly addressing the source of the problem. Environmental management is often impractical for the majority of horse owners. In fact, the pulmonary neutrophilia (inflammation) observed with both conditions is resistant to corticosteroid (Gold Standard for treatment) treatment and often persists in horses kept in antigen-rich environments. Bronchodilators (i.e. β-2 agonists) significantly reduce pulmonary resistance but do not alter airway hyperreactivity, and some horses can become resistant to the effects via downregulation of β2 receptors. Some may or may not have the benefit of increasing mucociliary clearance and possibly have anti-inflammatory effects. Phosphodiesterase inhibitors can be ineffective and mast cell stabilizers have variable efficacy. Therein lies the importance of this novel prophylactic and mitigative therapy to replace the current standard of treatment for which efficacy is variable and provides only symptomatic relief without addressing the primary multifactorial pathology. Other treatments, such as non-specific immune stimulants (such as α-Interferon and *Propionibacterium acnes*), mast cell inhibitors, and direct feeding of nutritional supplements to patient animals (such as antioxidants and omega-3-fatty acids), either stimulate the patient animal's immune system to clear any low level infections or aid in reduction of inflammation. Some treatments, such as those involving genetically engineered cytokines or mediators, are too focused and create an imbalance in the patient's immune system. This imbalance results in an increase of redundant factors that replace those initially targeted by the treatment.

BRIEF SUMMARY OF THE INVENTION

The present invention is generally directed to a method of making a blood product for administration to patient animals to prevent or mitigate a specific condition or disease. The method includes pre-treating one or more donor animals, collecting blood from the donor animals after pre-treatment, and processing the collected blood to make a blood product for administering to one or more patient animals. The pre-treatment step is designed to result in a blood product having an enhanced profile for preventing or mitigating a specific condition or disease. Recognizing that an animal's immune system is extraordinarily complex and there exists a significant amount of redundancy at the component, mechanism, and pathway levels, the term "enhanced profile" as used throughout the specification and claims, means that one or more beneficial components within the blood product that play a positive role in preventing or mitigating a specific condition have been increased and/or one or more undesirable components that play a negative role in preventing or treating a specific condition or disease (i.e. tend to cause or exacerbate the specific condition or disease) have been reduced.

In a preferred embodiment, the donor animal pre-treatment is designed to result in a purified and concentrated serum having an enhanced profile adapted to prevent or mitigate immune conditions or diseases by modulating a patient animal's immune system to combat inappropriate immune responses that result in exuberant and non-resolving inflammation. The pre-treatment includes a prescribed diet and/or an immunization regimen designed to optimize the blood levels of one or more components associated with healthy immune system response mechanisms that prevent or mitigate aberrant inflammation by selectively increasing the presence and concentration of preferred components (specific factors, antibodies, compounds, and the like) that play a positive role in healing, reducing and resolving inflammation and/or immunomodulation, and/or selectively reducing the presence and concentration of undesirable components that play a negative role in healing (i.e. exuberant inflammation), reducing and resolving inflammation and/or immunomodulation in the donor's blood. Specifically, the diet and/or immunization regimen are designed to increase the level of anti-inflammatory and pro-resolution components in the blood, while reducing the level of pro-inflammatory components without removing important defense mechanisms and causing disequilibrium in the immune system. This pre-treatment is designed to result in a natural blood product that effectively reduces or mitigates a variety of inflammatory disease conditions.

In one aspect of the invention, a pre-treatment diet lowers the protein to energy source ratio, where the energy source includes carbohydrates (starches and sugars) and fats. Preferably, the protein to energy ratio is reduced by approximately 10-15%. A preferred diet includes an increase in feedstuffs rich in fat and a concurrent decrease in carbohydrate load, which together decreases circulating pro-inflammatory cytokines in the blood product. More preferably, the fat component is largely supplied by an omega-3 fatty acid source (fish oil and tuna oil, for example) or a direct source of EPA and DHA, which further improves the anti-inflammatory profile and associated mediators, increases inflammatory resolution potential via pro-resolution mediators, and reduces the pro-inflammatory chemical mediators and cytokines, thereby optimizing the enhanced profile of the blood product for preventing and/or mitigating inappropriate inflammatory responses when administered to at-risk patient horses. Most preferably, the diet also includes antioxidant supplements (such as selenium, zinc, and vitamin E, astaxanthin, resveratrol, and others) to enhance antioxidant levels in the blood product, to counteract the increased level of free-radicals circulating in the donor's blood, and to offset free radicals introduced as a result of a high-fat diet. These dietary shifts reduce systemic inflammation and impact the presence of serum product proteins such as albumin and globulins.

In another aspect, a pre-treatment immunization regimen includes immunizations for one or more allergens, viral antigens, and/or bacterial antigens. This results in an increased production of antibodies capable of identifying or neutralizing allergens and antigens that would otherwise trigger an immune response resulting in inflammation.

In addition to diet and/or immunization, other variables are preferably adjusted to produce the designer blood product. These include the size of the donor group (a large group of donor animals is preferred), characteristics of the donor animals (donor animals are preferably selected from a wide variety of geographical areas and the majority of donors are young and healthy, i.e., do not exhibit symptoms of inflammation or other conditions or diseases and are at a healthy weight), the administration of certain supplements and/or stimulants to the donor animal, the administration of anti-inflammatory medicants (i.e. hyaluronic acid, glucosamine, chondroitin sulfate, avocado soy unsaponifiables, polysulfated glycosaminoglycans, pentosan phosphate, and methylsulfonylmethane) to the donor animal, the possible addition of certain stimulants to the collected blood prior to processing, and the elapsed time between blood collection and processing, and concentration of the final blood product. Adjusting one or more of the variables listed above may be considered part of the pre-treatment or method of pre-treating a donor animal as described herein.

After one to three months of pre-treatment, blood is collected from the donor animals and processed to create a designer blood product with an enhanced profile that effectively prevents or mitigates a variety of immune system diseases and conditions when administered to patient animals. As used throughout the specification and claims, the term "blood product" includes one or more of the following: whole blood, plasma, serum, red blood cells, white blood cells, platelets, blood extract, or blood derivative. In one aspect, the blood product is a serum that is preferably harvested 12-48 hours, most preferably after 24 hours, post-blood collection. The serum is concentrated and then provided to a patient animal in a localized area to provide passive support to the patient animal's immune system and modulate inflammation pathways. This multi-faceted and comprehensive approach supports the patient animal's immune system and encourages healthy inflammatory resolution to prevent/alleviate chronic inflammation and stop other inappropriate immune responses, including systemic inflammation.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

In a preferred embodiment, a method of pre-treatment for donor animals is designed to create a serum with an enhanced profile that supports a patient animal's immune system in achieving healthy homeostasis when administered locally. Specifically, the enhanced profile is designed to prevent or mitigate respiratory inflammation conditions and diseases in the patient animal, such as IAD in horses. The specific components present in the serum may act to inhibit, reduce, or resolve inflammation, provide repair and healing factors which modulate the effect of inflammation on surrounding cells and tissues, or stimulate certain inflammation pathways that are deficient but necessary.

Donor Animals

Before pre-treatment can begin, a plurality of blood donors are first identified using specific selection criteria. Preferably, the donors are of the same species as the patient animal. For example, a herd of mature horses is identified as donor stock for the production of equine serum. Animals selected for the donor herd should exhibit minimal evidence of systemic inflammatory conditions (such as osteoarthritis, Insulin Resistance, Equine Metabolic Syndrome, Cushings Disease, Equine Polysaccharide Storage Myopathy, Recurrent Airway Obstruction, muscle inflammation, Recurrent Rhabdomyolysis, laminitis, and hoof inflammation) or other conditions or diseases. The potential donor horses are screened by blood work analysis (complete blood count, chemistry profile, plasma fibrinogen, and serum amyloid, cytokines, iron, and total iron binding capacity) and physical examination. Only those horses having a healthy status will be selected for the donor group. Horses must also meet certain general blood donor qualifications before being added to the herd, including confirmation that they are free of blood factor A & Q antibodies, Equine Infectious Anemia (EIA), Equine Piroplasmosis (*Babesia theilleria* and *caballi*), *Brucellosis abortus*, Dourine (*Trypanosoma equiperdum*), Glanders (*Burkholderia mallei*), and Equine Viral Arteritis (AVA).

Preferably, the majority of the donor horses are mature (young to middle-age, i.e., 3-15 years of age), at a healthy weight, and in good body condition. In general, increased age and obesity have been associated with a low-grade systemic inflammatory response characterized by increased inflammatory cytokine concentrations in the blood. By selecting horses that are young and healthy, the level of undesirable components in the blood is reduced. After initial selection and during pre-treatment, it is generally desired that blood not be collected from horses later diagnosed with an illness, disease, or condition that could affect the enhanced profile of the blood product.

To achieve a high quality and consistent blood product, it is preferred that the donor group include a plurality of donor animals, preferably at least 2 donor animals, more preferably 50 or more animals, and most preferably 100 or more donor animals. Additionally, it is preferred that members of the donor group originate from a variety of geographic areas, preferably from at least two different geographical areas and most preferably from at least five different geographic areas, each area being at least 100 miles apart. The large number and variety in the origin of the donor horses enhances the profile of the serum product by increasing the spectrum of antibody coverage to the widest array of antigens, such as geographically distinct allergens, thereby maximizing protection and cross-protection capabilities, as well as the number of types and amount of additional preferred components present. The preferred donor horses are gelding draft horses to alleviate hormonal influences on the product. However, light or draft horse geldings, mares and/or stallions, including thoroughbred and quarter horses, may be used under certain circumstances to expand the diversity of the group and/or to selectively enhance the presence of certain components in the blood product that are associated with those horses.

Pooling in this manner takes advantage of each horse's individual genetic make-up and environmental experience. Once the donors are identified, they are typically brought to and maintained in a closed controlled donor herd at a single location for pre-treatment, albeit maintaining parts of the donor group at different locations, as well as maintaining a standing herd (as opposed to a closed herd), is contemplated within the scope of the invention.

Pre-Treatment Diet

In the preferred embodiment, the pre-treatment includes a prescribed diet. In general, the diet is a balanced diet appropriate for the expected level of blood production and includes "immunonutrition." Immunonutrition is the incorporation of specific immunomodulating nutrients, feedstuffs, and supplements into the diets of donor horses to modulate the desired immune system responses that will in turn result in an immunomodulating blood product that can be administered to recipient, at-risk horses for the prevention or mitigation of inappropriate immune responses, diseases, or conditions. Preferably, the diet minimizes the amount of feedstuffs containing high proportions of omega-6 fatty acids and sugars and starches and maximizes the amount of feedstuffs containing omega-3 polyunsaturated fatty acids and fiber. More preferably, the diet includes specific immunomodulating nutrients and supplements including glutamine, arginine, cysteine/methionine, zinc, selenium, vitamin A, lycopene and lutein, vitamin E, vitamin C, omega-3 polyunsaturated fatty acids, and antioxidants, as well as others. Amino acid profiles of certain proteins are selected to manipulate immune responses. Selenium supplementation enhances immune system function and stimulates an increase in the levels of immunoglobulins and improves vaccine response. Oligosaccharide diet supplementation also enhances defensive immune responses and attenuates allergic responses. Certain herbs, such as ginseng, yucca, and ginger are known to inhibit pro-inflammatory cytokine production and to have anti-inflammatory and antioxidant properties. Immunonutrition may also include incorporation of allergens, antibodies, or probiotics into the diet.

Preferably, the base diet for the blood donor herd is formulated to the nutrient requirements for horses performing a light to moderate workload to account for the production requirements of donating a large volume of blood on a regular basis. Though blood harvesting nutrient requirements have not been scientifically determined for equine blood donors, the anabolic work required to rebuild and replenish vital blood components including red blood cells and protein that are removed during blood harvesting, while maintaining overall health by providing appropriate energy sources and nutrients needs to be taken into account. Special attention may be given to nutrients that in specific combinations promote red blood cell recovery and include but are not limited to iron, folic acid, vitamin B12, cobalt, copper, and zinc. A balanced diet is central in accounting for blood production, but specific consideration of the proper protein and energy ratios is also important as the diet should not create a nutrient imbalance that may result in poor nutrient utilization, poor feed efficiency, metabolic disorders, and possible organ damage. In the preferred embodiment, the energy sources are selected to fulfill blood regenerating requirements while concurrently increasing the production or presence of preferred immunomodulating components and decrease the production or presence of undesirable components in the blood, and thus the final serum product.

Typical equine diets are largely composed of cereal grains and are low in fat (2-4%). However, diets containing significant amounts of cereal grains often elevate the level of available soluble carbohydrates (i.e. starch) to the horse. This in turn can be detrimental to the horse by resulting in increased production of pro-inflammatory cytokine profiles that contribute to subclinical systemic inflammation.

Research has demonstrated the effectiveness of high-fat diets for horses. The fat content of these diets generally range between 6-10%, although a horse can tolerate up to 20% in a diet. The advantage of a high-fat diet is that the horse is better adapted to utilizing fat as an energy source as opposed to cereal grains. This is primarily due to the absence of a gall bladder and the continuous secretion of bile. Animal fats (unsaturated fats) and vegetable fats (primarily polyunsaturated oils) are common fat sources used in equine diets, although vegetable oils are preferred as they are more palatable and bioavailable. In fact, 85-95% of the fats are digested and absorbed in the small intestine where only 50-60% of cereal grains are digested and absorbed there. Increased digestion and absorption in the small intestine means less fermentation in the hindgut, which in turn leaves more energy available for work and the production of blood serum or even milk in lactating females. By reducing the amount of soluble carbohydrates reaching the hindgut of the horse, the proprionate:acetate ratio of volatile fatty acids in the hindgut and death rate of healthy bacterial flora is lowered. A healthier gut reduces the detrimental production and absorption of endotoxins/exotoxins associated with gut inflammation and the subsequent increased production of pro-inflammatory cytokines. Therefore, replacing a portion of the rapidly fermentable carbohydrate energy source (in the form of cereal grain) with an equivalent or isocaloric amount of a more energy-dense fat source, will improve feed efficiencies, nutrient digestion, and metabolism resulting in a healthier horse. This nutritional approach will help reduce the occurrence of systemic inflammation and disease and provide better blood product quality and quantity.

Increased dietary fat (i.e. vegetable oils) has been shown to decrease the predisposition and susceptibility of a horse to inflammatory conditions, including Recurrent Exertional Rhabdomyolysis or "tying-up," Polysaccharide Storage Myopathy, gut inflammation/colic, endotoxemia, gastric ulcers, Equine Metabolic Syndrome, Cushings, hyperglycemia, hyperinsulinemia, insulin resistance, systemic inflammation, osteoarthritis, Osteochondritis Dessicans, and laminitis. If any of these conditions are present in the donor herd, it could negatively impact the serum product quality. Fat supplementation has also been demonstrated to allow better thermal regulation and heat dissipation in hot and humid summer month environments (less heat stress).

There are no "bad oils" and in fact, horses must consume essential fatty acids, specifically linoleic acid (LA or omega-6) and alpha-linolenic acid (ALA or omega-3), because their bodies lack the enzymes needed to synthesize them. Several biological processes require essential fatty acids for conversion via elongation and desaturation into biologically active longer chain fatty acids for the maintenance of cell membrane fluidity and stability, development and function of brain and nerve tissue, oxygen transfer and energy production, immune functions, and conversion of compounds involved in all body functions (i.e. hormones).

It is recommended that the dietary dry matter in an equine diet include at least 0.5% linoleic acid (an omega-6 fatty acid). This minimal level of omega-6 fatty acid is necessary to fight infections and to mount appropriate immune responses (such as healing), but supplementation must be balanced since omega-6 fatty acids compete with the omega-3 fatty acids, which results in an increased amount of endogenous pro-inflammatory agents when omega-6 fatty acids predominate. For example, largely cereal grain-based diets can further increase the omega-6:omega-3 ratio in an undesirable direction (i.e. 8:1 to 17.5:1), as can omega-6 predominant vegetable oils such as corn oil that have ratios in the range of 57-84:1.

Therefore, excessive omega-6 fatty acids contribute to exuberant inflammation and reduced cell-mediated immunity, whereas omega-3 fatty acids are potent anti-inflammatory agents that help achieve homeostasis between pro-inflammatory and anti-inflammatory mediators. Ratios of Arachidonic Acid (an omega-6 fatty acid):Docosahexaenoic Acid (DHA; an omega-3 fatty acid) of 1:1 and 2:1 have been demonstrated to minimize pro-inflammatory responses (i.e., NF-KB, TNF-α, IL-6, and IL-8 and pro-inflammatory mediators such as leukotrienes and prostaglandins) and enhance anti-inflammatory responses (i.e., IL-10). Fat sources that have low omega-6:omega-3 ratios (4:1 to 7:1), such as soybean oil (7:1) canola oil (2-3:1), linseed, and flaxseed oil are superior supplements because they supply a larger proportion of the omega-3 fatty acid, such as ALA.

Although the high level of ALA in these favorable vegetable oils is beneficial, the ALA is slowly and inefficiently converted to the desired longer chain omega-3 fatty acids such as eicosapentaenoic acid (EPA) and docosahexaenoic acid (DHA) by the horse. As a result, these sources may not alter the omega-6:omega-3 ratio and amounts of the critical and biologically active longer chain omega-3 fatty acids in the circulation. Although the ideal omega-6:omega-3 ratio for horses has not been determined, health benefits have been observed between the ranges of 1:1 and 10:1. Therefore, docosahexaenoic acid and eicosapentaenoic acid levels are optimized in the embodiment with the addition of marine fish oils (i.e. Menhaden, sardine, cod, mackerel, and anchovy oil) hill oil, or an algal product with an approximate DHA:EPA ratio of 1:1.5.

Specific omega-3 fat supplementation in the direct form of EPA and DHA in mammalian diets provides many health benefits in addition to those realized with generic fat or ALA supplementation alone. These include, but are not limited to blood vessel compliance, red blood cell deformability, increased red blood cell counts, and decreased insulin resistance, as well as additional beneficial effects on the cardiovascular, respiratory, gastrointestinal, musculo skeletal, integument, reproductive, and nervous systems. Generally, omega-3 fatty acids (specifically DHA and EPA) have been shown to decrease inflammatory cell (neutrophil and macrophage) recruitment/activation, infiltration, and accumulation (overall lung inflammation), enhance alveolar macrophage phagocytic activity and clearance of dead neutrophils and antigens, decrease pro-inflammatory cytokines/chemokines, increase anti-inflammatory cytokines/chemokines and other mediators, influence signal transduction pathways to alter protein expression of inflammatory mediators, alter lymphocyte populations and the consequent mediators that are produced, decrease metalloproteinase enzymes (MMPs), block pro-inflammatory responses of dendritic cells, decrease responsiveness to allergens, decrease mucus production, decrease pro-inflammatory eicosanoids (2 and 4 series) and increase production of their anti-inflammatory counterparts (3 and 5 series) through cell/tissue membrane composition alteration, and decrease IgE production, while consequently decreasing tissue damage, improving lung function, and decreasing airway hyper-responsiveness. Moreover, the increased amount of EPA and DHA in the donor's prescribed diet, results in the formation of resolution mediators, such as protectins, lipoxins, maresins, and resolvins, which quickly signal the resolution of inappropriate inflammation. Omega-3 supplemented diets have additionally been shown to decrease fibrinogen (one of the most sensitive indicators of inflammation in a horse) and other acute phase proteins, support normal immune function, increase antibody response to vaccination, decrease intracellular inflammatory signaling pathways, provide anti-fibrotic (scaring) activity, and increase antioxidant capability (decrease oxidant stress), so that less tissue damage is incurred.

The preferred supplemental dose of EPA and DHA in the embodiment may range from 60 mg/kg of combined DHA and EPA multiplied by the metabolic body weight ((body weight in kg)$^{0.75}$) of the horse (for example, 9 g of EPA+DHA/horse/day) to 65 mg/kg of combined DHA and EPA (for example, 60 g EPA+DHA/horse/day). Ratios of EPA:DHA have typically been in the range of 1-1.5:1, but could vary widely from 1:5 to 5:1. This dose is much higher than those commercially and currently available in the industry by three to fifteen fold. The metabolic response in the horse from different sources (fish or algal) of DHA and EPA will need to be taken into consideration. A preferred omega-3 supplemented diet includes a combined dose of EPA and DHA of approximately 64.4 mg/kg of body weight per day. For instance, if the average donor horse weighs 821 kg and receives a diet supplemented with a EPA:DHA ratio of 1:1, that horse would consume approximately 52.8 g total and 26.4 g each of EPA and DHA.

In the preferred embodiment, the donor's diet also includes antioxidant nutriceutical supplementation. Preferred antioxidant nutriceuticals may include microminerals (zinc, copper, and manganese, for example), vitamin E, vitamin C, astaxanthin, resveratrol, medicinal mushrooms (e.g., an EQUINE MATRIX™ product, available through Mushroom Matrix located at 2033 Marilyn Lane, Suite B, San Marcos, Calif. 92069, containing Cordyceps Militaris, Reishi, Antrodia, Agaricus blazel, Maitake, Shiltake, King Trumpet (L-ergothioneine), and Beech), selenium, lipoic acid, hypoic acid, β-carotene, and grape seed extract. Increasing the amount of antioxidant nutriceuticals in the donor's diet further contributes to the level of available resolution mediators in the donor horse's blood stream. This reduces tissue damage by enhancing antioxidant defenses, and by reducing inflammatory response and consequent production of inflammatory mediators. Pretreatment elevates antioxidant levels and antioxidant markers while decreasing oxidative stress markers.

The basic nutrient requirements for a blood donor horse of average size (848 kg) would be similar to a horse having a light to moderate workload as shown in Table 1 below.

TABLE 1

Nutrient requirements based on workload for the average horse size (848 kg)

|  | DE (Mcal/d) | CP (g) | Ca (g) | P (g) | Fe (mg) | Vit. E (IU) |
|---|---|---|---|---|---|---|
| Maintenance (Avg.) | 28.26 | 1068.19 | 33.91 | 23.74 | 678 | 840 |
| Workloads: | | | | | | |
| Light | 33.91 | 1185.94 | 50.87 | 30.52 | 678 | 1356 |
| Moderate | 39.56 | 1301.80 | 59.34 | 35.61 | 763 | 1526 |
| Heavy | 45.21 | 1461.00 | 67.82 | 49.17 | 847 | 1695 |
| Very Heavy | 58.50 | 1703.08 | 67.82 | 49.17 | 847 | 1695 |

The nutrient composition of several preferred pre-treatment diets in accordance with the present invention as compared to a control diet is shown in Table 2 below on a dry matter basis.

TABLE 2

Nutrient composition of preferred pre-treatment diets on a dry matter basis

| | | | Preferred Diets | | | | |
| | Control | | Canola Oil | | Fish Oil | | |
| Item | Pellet | Alfalfa hay | LSMF Pellet | MSHF Pellet | E:D1:1 Pellet | E:D2:1 Pellet | Alfalfa Hay |
|---|---|---|---|---|---|---|---|
| DM (%) | 91.56 | 90.32 | 89.08 | 88.51 | 92.31 | 93.08 | 89.64 |
| DE (Mcal/kg) | 2.93 | 2.37 | 2.55 | 2.78 | 2.79 | 2.84 | 2.48 |
| (Mcal/lb) | 1.33 | 1.08 | 1.16 | 1.26 | 1.27 | 1.29 | 1.13 |

TABLE 2-continued

Nutrient composition of preferred pre-treatment diets on a dry matter basis

|  | Control | | Preferred Diets | | | | |
|---|---|---|---|---|---|---|---|
|  | | | Canola Oil | | Fish Oil | | |
| Item | Pellet | Alfalfa hay | LSMF Pellet | MSHF Pellet | E:D1:1 Pellet | E:D2:1 Pellet | Alfalfa Hay |
| Total Fat (%) | 4.54 | *1.29* | 5.68 | 7.34 | 6.83 | 6.74 | 1.32 |
| Ether Extract (%) | 4.76 | 2.44 | 7.14 | 9.44 | 9.25 | 9.06 | 2.47 |
| Starch (%) | *15.90* | *1.57* | 11.27 | 16.30 | 15.96 | 18.51 | 0.64 |
| Sugar (%) | *7.80* | 8.96 | 6.81 | 6.93 | 6.34 | 7.11 | 6.21 |
| Nonfibrous CHO (NFC), % | *39.00* | *24.30* | *24.47* | *27.06* | *27.69* | *29.55* | *30.24* |
| Crude Protein (%) | 16.68 | 23.41 | 14.90 | 14.41 | 15.00 | 15.07 | 21.17 |
| Acid Detergent fiber (%) | 12.83 | 30.89 | 24.44 | 19.71 | 18.80 | 17.79 | 26.62 |
| Neutral Detergent fiber (%) | 31.63 | 36.29 | 42.75 | 39.58 | 38.39 | 36.65 | 33.99 |
| Hemicellulose (%) | 18.80 | 8.00 | 18.31 | 19.87 | 19.59 | 18.86 | 7.37 |
| Ash (%) | 8.14 | 13.56 | 10.74 | 9.51 | 9.67 | 9.67 | 13.18 |
| Calcium (Ca) (%) | 1.42 | 1.72 | 1.57 | 1.56 | 1.75 | 1.74 | 1.80 |
| Phosphorus (P) (%) | 0.83 | 0.27 | 1.07 | 1.09 | 1.22 | 1.22 | 0.29 |
| Magnesium (Mg), % | 0.42 | 0.26 | 0.51 | 0.45 | 0.45 | 0.49 | 0.27 |
| Potassium (K) (%) | 1.29 | 2.85 | 1.49 | 1.45 | 1.58 | 1.57 | 3.35 |
| Sulfur (S) (%) | — | 0.15 | 0.31 | 0.24 | 0.25 | 0.25 | 0.40 |
| Sodium (Na) (%) | — | 0.06 | 0.76 | 0.29 | 0.39 | 0.34 | 0.06 |
| Manganese (Mn) (ppm) | *237.55* | *59.00* | 249.00 | 273.00 | 277.00 | 259.00 | 74.00 |
| Zinc (Zn) (ppm) | *224.68* | *28.00* | 216.0 | 229.00 | 262.00 | 271.00 | 50.00 |
| Copper (Cu) (ppm) | *52.84* | *7.00* | 50.00 | 52.00 | 55.00 | 54.00 | 7.00 |
| Iron (Fe) (ppm) | *164.31* | *242.00* | 497.00 | 418.00 | 494.00 | 521.00 | 242.00 |
| Selenium (Se) (ppm) | *0.60* | *0.20* | *0.67* | *0.67* | *0.67* | *0.67* | *0.20* |
| Molybdenum (Mo) (ppm) | — | 1.35 | 1.46 | 1.53 | 1.68 | 1.59 | 1.35 |
| Vitamin A (KIU/lb min) | *8.70* | *13.30* | *5.78* | *5.78* | *5.78* | *5.78* | *13.30* |
| Vitamin E (IU/lb), min | 63.44 | 40.00 | 199.9 | 200.2 | 200.2 | 200.2 | 40.00 |

In general, the LSMF pellet has a low starch, moderate fat content, the MSHF pellet has a moderate starch, high fat content, the E:D1:1 pellet has a 1:1 EPA:DHA ratio, and the E:D2:1 pellet has a 2:1 EPA:DHA ratio. Donors fed one of the LSMF, MSHF, E:D1:1, and E:D2:1 type pellets were also fed the Alfalfa hay component. The numbers in italics in Table 2 are calculated values.

The fatty acid composition of each diet component is shown in Table 3 below on a dry matter basis. Each of the fatty acid components is expressed as a percentage of total fat.

TABLE 3

Fatty acid composition of preferred pre-treatment diets on a dry matter basis

|  | Control | | Preferred Diets | | | | |
|---|---|---|---|---|---|---|---|
|  | | | Canola Oil | | Fish Oil | | |
| Item | Pellet | Alfalfa hay | LSMF Pellet | MSHF Pellet | E:D1:1 Pellet | E:D2:1 Pellet | Alfalfa hay |
| Total Fat (%) | 4.54 | 1.29 | 5.68 | 7.34 | 6.83 | 6.74 | 1.32 |
| Total Unsaturated FA, % | 80.83 | 62.57 | 87.26 | 88.49 | 68.61 | 68.31 | 62.57 |
| Polyunsaturated FA, % | 57.05 | 50.01 | 47.75 | 44.66 | 45.39 | 45.36 | 50.01 |
| Monounsaturated FA, % | 23.78 | 12.56 | 39.51 | 43.83 | 23.22 | 22.95 | 12.56 |
| Saturated FA, % | 19.17 | 37.43 | 12.74 | 11.51 | 31.39 | 31.69 | 37.43 |
| Omega 3, % | 4.72 | 35.67 | 6.63 | 7.24 | 16.30 | 15.43 | 36.51 |
| Omega 6, % | 52.33 | 13.50 | 41.12 | 37.42 | 29.09 | 29.93 | 13.50 |
| Linoleic (18:2), % | 52.33 | 13.50 | 41.12 | 37.42 | 28.57 | 29.49 | 13.50 |
| α-Linolenic (18:3), % | 4.72 | 35.67 | 6.63 | 7.24 | 3.11 | 3.27 | 36.51 |
| Arachidic (20:0), % | 0.29 | 1.16 | 0.55 | 0.54 | 1.57 | 1.57 | 1.16 |
| Arachidonic (20:4), % | 0.00 | 0.00 | 0.00 | 0.00 | 0.52 | 0.44 | 0.00 |
| Eicosapentaenoic (20:5), % | 0.00 | 0.00 | 0.00 | 0.00 | 6.86 | 6.79 | 0.00 |
| Docosapentaenoic (22:5), % | 0.00 | 0.00 | 0.00 | 0.00 | 0.00 | 0.00 | 0.00 |
| Docosahexaenoic (22:6), % | 0.00 | 0.00 | 0.00 | 0.00 | 6.17 | 5.20 | 0.00 |

The percent concentration difference for each of the preferred diet pellet components as compared to the control diet pellet component is shown below in Tables 4 and 5.

TABLE 4

Percent differences in preferred pre-treatment concentrate components compared to control concentrate components

| | Preferred Diets | | | |
|---|---|---|---|---|
| | Canola Oil | | Fish Oil | |
| Item | LSMF | MSHF | E:D1:1 | E:D2:1 |
| DM, % | -2.71% | -3.33% | 0.82% | 1.66% |
| DE (Mcal/kg) | -12.97% | -5.12% | -4.78% | -3.07% |
| (Mcal/lb) | -12.78% | -5.26% | -4.51% | -3.01% |
| Total Fat (%) | 25.11% | 61.67% | 50.44% | 48.46% |
| Ether Extract (%) | 50.00% | 98.32% | 94.33% | 90.34% |
| Starch (%) | -29.12% | 2.52% | 0.38% | 16.42% |
| Sugar (%) | -12.69% | -11.15% | -18.72% | -8.85% |
| Nonfibrous CHO (NFC), % | -37.26% | -30.62% | -29.00% | -24.23% |
| Crude Protein (%) | -10.67% | -13.61% | -10.07% | -9.65% |
| Acid Detergent fiber (%) | 90.49% | 53.62% | 46.53% | 38.66% |
| Neutral Detergent fiber (%) | 35.16% | 25.13% | 21.37% | 15.87% |
| Hemicellulose (%) | -2.61% | 5.69% | 4.20% | 0.32% |
| Ash (%) | 31.94% | 16.83% | 18.80% | 18.80% |
| Calcium (Ca), % | 10.56% | 9.86% | 23.24% | 22.54% |
| Phosphorus (P), % | 28.92% | 31.33% | 46.99% | 46.99% |
| Magnesium (Mg), % | 21.43% | 7.14% | 7.14% | 16.67% |
| Potassium (K), % | 15.50% | 12.40% | 22.48% | 21.71% |
| Sulfur (S), % | NA | NA | NA | NA |
| Sodium (Na), % | NA | NA | NA | NA |
| Manganese (Mn), ppm | 4.82% | 14.92% | 16.61% | 9.03% |
| Zinc (Zn), ppm | -3.86% | 1.92% | 16.61% | 20.62% |
| Copper (Cu), ppm | -5.37% | -1.59% | 4.09% | 2.20% |
| Iron (Fe), ppm | 202.48% | 154.40% | 200.65% | 217.08% |
| Selenium (Se), ppm | 11.67% | 11.67% | 11.67% | 11.67% |
| Molybdenum (Mo), ppm | NA | NA | NA | NA |
| Vitamin A (KIU/lb), min | -33.56% | -33.56% | -33.56% | -33.56% |
| Vitamin E (IU/lb), min | 215.10% | 215.57% | 215.57% | 215.57% |

TABLE 5

Percent differences in preferred pre-treatment concentrate fatty acid components compared to control concentrate fatty acid components

| | Preferred Diets | | | |
|---|---|---|---|---|
| | Canola Oil | | Fish Oil | |
| Item | LSMF | MSHF | E:D1:1 | E:D2:1 |
| Total Fat (%) | 25.11% | 61.67% | 50.44% | 48.46% |
| Total Unsaturated FA, % | 7.95% | 9.48% | -15.12% | -15.49% |
| Polyunsaturated FA, % | -16.30% | -21.72% | -20.44% | -20.49% |
| Monounsaturated FA, % | 66.15% | 84.31% | -2.35% | -3.49% |
| Saturated FA, % | -33.54% | -39.96% | 63.75% | 65.31% |
| Omega 3, % | 40.47% | 53.39% | 245.34% | 226.91% |
| Omega 6, % | -21.42% | -28.49% | -44.41% | -42.81% |
| Linoleic (18:2), % | -21.42% | -28.49% | -45.40% | -43.65% |
| α-Linolenic (18:3), % | 40.47% | 53.39% | -34.11% | -30.72% |
| Arachidic (20:0), % | 89.66% | 86.21% | 441.38% | 441.38% |
| Arachidonic (20:4), % | | | | |
| Eicosapentaenoic (20:5), % | | | | |
| Docosapentaenoic (22:5), % | 0.00% | 0.00% | 0.00% | 0.00% |
| Docosahexaenoic (22:6), % | | | | |

The daily nutrient intake attributable to the pellet component for a donor horse on the control diet as compared to a donor horse on one of the preferred diets is shown in Table 6 below on a dry matter basis, and the total daily nutrient intake for a donor horse on the control diet as compared to a donor horse on the preferred diets on a per 100 kg body weight dry basis is shown in Table 7.

TABLE 6

Daily nutrient concentrate intakes for control and preferred pre-treatment diets on a dry matter base

| | | Preferred Diets | | | |
|---|---|---|---|---|---|
| | | Canola Oil | | Fish Oil | |
| Item | Control | LSMF | MSHF | E:D1:1 | E:D2:1 |
| DM, lbs | 7.32 | 8.91 | 8.85 | 9.23 | 9.31 |
| DM, kg | 3.33 | 4.05 | 4.02 | 4.20 | 4.23 |
| DE, Mcal | 9.76 | 10.33 | 11.18 | 11.71 | 12.02 |
| Total Fat, g | 151.16 | 229.99 | 295.30 | 286.58 | 285.16 |
| Ether Extract, g | 158.48 | 289.11 | 379.79 | 388.12 | 383.32 |
| Starch, g | 529.38 | 456.33 | 655.78 | 669.67 | 783.14 |
| Sugar, g | 259.70 | 275.74 | 278.81 | 266.02 | 300.82 |
| Starch and Sugar, g | 789.08 | 732.08 | 934.59 | 935.69 | 1083.96 |
| Nonfibrous CHO, g | 1298.49 | 990.81 | 1088.67 | 1161.85 | 1250.23 |
| Crude Protein, g | 555.35 | 603.31 | 579.74 | 629.39 | 637.60 |
| Crude Protein:Energy ratio, g/Mcal | 56.93 | 58.43 | 51.83 | 53.76 | 53.06 |
| Crude fiber, max, g | 326.29 | 415.44 | 304.55 | 317.63 | 320.28 |
| Acid Detergent fiber, g | 427.17 | 989.60 | 792.97 | 788.83 | 752.68 |
| Neutral Detergent fiber, g | 1053.11 | 1730.99 | 1592.38 | 1610.81 | 1550.63 |
| Hemicellulose, g | 625.94 | 741.39 | 799.41 | 821.98 | 797.95 |
| Ash, g | 271.02 | 434.87 | 382.60 | 405.74 | 409.13 |
| Calcium, g | 47.28 | 63.57 | 62.76 | 73.43 | 73.62 |
| Phosphorus, g | 27.63 | 43.33 | 43.85 | 51.19 | 51.62 |
| Potassium, g | 42.95 | 60.33 | 58.34 | 66.30 | 66.43 |
| Magnesium, g | 13.98 | 20.65 | 18.10 | 18.88 | 20.73 |
| Selenium, mg | 2.00 | 2.71 | 2.70 | 2.81 | 2.83 |
| Zinc, mg | 748.06 | 874.60 | 921.31 | 1099.33 | 1146.58 |
| Manganese, mg | 790.75 | 1008.22 | 1098.33 | 1162.27 | 1095.81 |
| Iron, mg | 807.26 | 2012.40 | 1681.69 | 2072.78 | 2204.30 |
| Copper, mg | 173.13 | 202.45 | 209.21 | 230.78 | 228.47 |
| Vitamin A, KIU | 63.73 | 51.49 | 51.16 | 53.36 | 53.80 |
| Vitamin E, IU | 464.69 | 1780.71 | 1771.97 | 1848.05 | 1863.46 |

TABLE 7

Total daily nutrient intakes for control and preferred pre-treatment diets on a dry matter base per 100 kg live body weight

| | | Preferred Diets | | | |
|---|---|---|---|---|---|
| | Control | Canola Oil | | Fish Oil | |
| Item | Diet | LSMF | MSHF | E:D1:1 | E:D2:1 |
| DM, lbs | 3.27 | 3.44 | 3.45 | 3.43 | 3.44 |
| DM, kg | 1.49 | 1.56 | 1.57 | 1.56 | 1.57 |
| DE, Mcal | 3.74 | 3.91 | 4.04 | 4.02 | 4.06 |
| Total Fat, g | 31.91 | 41.39 | 49.43 | 47.49 | 47.33 |
| Ether Extract, g | 45.34 | 60.84 | 72.01 | 71.64 | 71.08 |
| Starch, g | 79.52 | 60.64 | 84.70 | 84.74 | 97.93 |
| Sugar, g | 128.54 | 99.88 | 100.95 | 97.59 | 101.63 |
| Starch and Sugar, g | 208.06 | 160.52 | 185.65 | 182.33 | 199.57 |
| Nonfibrous CHO, g | 418.59 | 444.97 | 459.73 | 459.68 | 469.96 |
| Crude Protein, g | 321.33 | 300.88 | 300.23 | 300.41 | 301.37 |
| CP:Energy ratio, g/Mcal[a] | 85.92 | 76.99 | 74.36 | 74.67 | 74.25 |
| Crude fiber, g | 257.07 | 173.65 | 161.75 | 160.26 | 160.57 |
| Acid Detergent fiber, g | 388.01 | 405.51 | 385.10 | 377.45 | 373.25 |
| Neutral Detergent fiber, g | 520.77 | 572.77 | 560.42 | 552.14 | 545.14 |
| Ash, g | 180.16 | 194.29 | 189.48 | 188.65 | 189.04 |
| Calcium, g | 24.37 | 27.03 | 27.12 | 27.86 | 27.88 |
| Phosphorus, g | 6.21 | 8.25 | 8.37 | 9.07 | 9.11 |
| CA:P ratio | 3.93:1 | 3.28:1 | 3.24:1 | 3.07:1 | 3.06:1 |
| Potassium, g | 36.22 | 8.25 | 8.37 | 43.67 | 43.68 |
| Magnesium, g | 4.49 | 5.36 | 5.10 | 5.09 | 5.31 |
| Selenium, mg | 0.45 | 0.54 | 0.54 | 0.54 | 0.54 |

TABLE 7-continued

Total daily nutrient intakes for control and preferred pre-treatment diets on a dry matter base per 100 kg live body weight

| | Control Diet | Preferred Diets | | | |
|---|---|---|---|---|---|
| | | Canola Oil | | Fish Oil | |
| Item | | LSMF | MSHF | E:D1:1 | E:D2:1 |
| Zinc, mg | 118.72 | 157.19 | 163.85 | 181.50 | 186.99 |
| Manganese, mg | 157.64 | 198.98 | 211.07 | 214.58 | 206.85 |
| Iron, mg | 359.64 | 499.56 | 463.93 | 500.77 | 516.07 |
| Copper, mg | 28.04 | 31.42 | 32.44 | 34.35 | 34.08 |
| Vitamin A, KIU | 39.49 | 37.83 | 38.06 | 37.61 | 37.66 |
| Vitamin E, IU | 150.94 | 305.06 | 306.20 | 309.34 | 311.14 |

[a]Total allotment of Crude Protein:Energy ratio in g/Mcal per day

The fatty acid composition of the daily nutrient intake attributable to the pellet component of each diet is shown in Table 8 below on a dry matter basis, and the total daily fatty acid nutrient intake for the control and the preferred diets on a per 100 kg body weight basis is shown in Table 9.

TABLE 8

Daily fatty acid concentrate intakes for control and preferred pre-treatment diets on a dry matter base

| | | Preferred Diets | | | |
|---|---|---|---|---|---|
| | | Canola Oil | | Fish Oil | |
| Item | Control | LSMF | MSHF | E:D1:1 | E:D2:1 |
| Total Fat, g | 151.16 | 229.99 | 295.30 | 286.58 | 285.16 |
| Total Unsaturated FA, g | 122.18 | 200.69 | 261.31 | 196.62 | 194.80 |
| Polyunsaturated FA, g | 86.24 | 109.82 | 131.88 | 130.08 | 129.35 |
| Monounsaturated FA, g | 35.95 | 90.87 | 129.43 | 66.54 | 65.44 |
| Saturated FA, g | 28.98 | 29.30 | 33.99 | 89.96 | 90.37 |
| Omega 3, g | 7.13 | 15.25 | 21.38 | 46.71 | 44.00 |
| Omega 6, g | 79.10 | 94.57 | 110.50 | 83.37 | 85.35 |
| Linoleic (18:2), g | 79.10 | 94.57 | 110.50 | 81.88 | 84.09 |
| α-Linolenic (18:3), g | 7.13 | 15.25 | 21.38 | 8.91 | 9.32 |
| Arachidic (20:0), g | 0.44 | 1.26 | 1.59 | 4.50 | 4.48 |
| Arachidonic (20:4), g | 0.00 | 0.00 | 0.00 | 1.49 | 1.25 |
| Eicosapentaenoic (20:5), g | 0.00 | 0.00 | 0.00 | 19.66 | 19.36 |
| Docosapentaenoic (22:5), g | 0.00 | 0.00 | 0.00 | 0.00 | 0.00 |
| Docosahexaenoic (22:6), g | 0.00 | 0.00 | 0.00 | 17.68 | 14.83 |
| Total EPA and DHA, g | | | | 37.34 | 34.19 |

TABLE 9

Daily fatty acid concentrate intakes for control and preferred pre-treatment diets on a dry matter basis per 100 kg live body weight

| | Control Diet | Preferred Diets | | | |
|---|---|---|---|---|---|
| | | Canola Oil | | Fish Oil | |
| Item[a] | | LSMF | MSHF | E:D1:1 | E:D2:1 |
| Total Fat, g | 17.89 | 27.22 | 34.95 | 33.91 | 33.75 |
| Total Unsaturated FA, g | 14.46 | 23.75 | 30.92 | 23.27 | 23.05 |
| Polyunsaturated FA, g | 10.21 | 13.00 | 15.61 | 15.39 | 15.31 |
| Monounsaturated FA, g | 4.25 | 10.75 | 15.32 | 7.88 | 7.74 |
| Saturated FA, g | 3.43 | 3.47 | 4.02 | 10.65 | 10.69 |
| Omega 3, g | 0.84 | 1.80 | 2.53 | 5.53 | 5.21 |
| Omega 6, g | 9.36 | 11.19 | 13.08 | 9.87 | 10.10 |
| Omega 6:3 ratio | 11.09:1 | 6.20:1 | 5.17:1 | 1.78:1 | 1.94:1 |

TABLE 9-continued

Daily fatty acid concentrate intakes for control and preferred pre-treatment diets on a dry matter basis per 100 kg live body weight

| | Control Diet | Preferred Diets | | | |
|---|---|---|---|---|---|
| | | Canola Oil | | Fish Oil | |
| Item[a] | | LSMF | MSHF | E:D1:1 | E:D2:1 |
| Linoleic (18:2), g | 9.36 | 11.19 | 13.08 | 9.69 | 9.95 |
| α-Linolenic (18:3), g | 0.84 | 1.80 | 2.53 | 1.05 | 1.10 |
| Arachidic (20:0), g | 0.05 | 0.15 | 0.19 | 0.53 | 0.53 |
| Arachidonic (20:4), g | 0.00 | 0.00 | 0.00 | 0.18 | 0.15 |
| Eicosapentaenoic (20:5), g | 0.00 | 0.00 | 0.00 | 2.33 | 2.29 |
| Docosapentaenoic (22:5), g | 0.00 | 0.00 | 0.00 | 0.00 | 0.00 |
| Docosahexaenoic (22:6), g | 0.00 | 0.00 | 0.00 | 2.09 | 1.75 |
| Total EPA and DHA, g | 0.00 | 0.00 | 0.00 | 4.42 | 4.05 |
| EPA:DHA ratio | | | | 1.11:1 | 1.31:1 |

The percent difference in daily nutrient intake attributable to each of the preferred diet pellets as compared to the control diet pellet is shown below in Tables 10 and 11.

TABLE 10

Percent differences in preferred pre-treatment concentrate intake of nutrient components compared to control intake of nutrient concentrate components

| | Preferred Diets | | | |
|---|---|---|---|---|
| | Canola Oil | | Fish Oil | |
| Item | LSMF | MSHF | E:D1:1 | E:D2:1 |
| DM, lbs | 21.6% | 20.8% | 26.0% | 27.1% |
| DM, kg | 21.6% | 20.8% | 26.0% | 27.1% |
| DE, Mcal | 5.8% | 14.6% | 20.0% | 23.2% |
| (Mcal/lb) | 6.1% | 14.5% | 20.3% | 23.3% |
| Total Fat, g | 52.2% | 95.4% | 89.6% | 88.7% |
| Ether Extract, g | 82.4% | 139.6% | 144.9% | 141.9% |
| Starch, g | −13.8% | 23.9% | 26.5% | 47.9% |
| Sugar, g | 6.2% | 7.4% | 2.4% | 15.8% |
| Starch and Sugar, g | −7.2% | 18.4% | 18.6% | 37.4% |
| NFC, g | −23.7% | −16.2% | −10.5% | −3.7% |
| C P,g | 8.6% | 4.4% | 13.3% | 14.8% |
| Crude Protein:Energy ration, g/Mcal | 2.6% | −8.9% | −5.6% | −6.8% |
| Crude fiber, max, g | 27.3% | −6.7% | −2.7% | −1.8% |
| Acid Detergent fiber, g | 131.7% | 85.6% | 84.7% | 76.2% |
| Neutral Detergent fiber, g | 64.4% | 51.2% | 53.0% | 47.2% |
| Hemicellulose, g | 18.4% | 27.7% | 31.3% | 27.5% |
| Ash, g | 60.5% | 41.2% | 49.7% | 51.0% |
| Calcium, g | 34.5% | 32.7% | 55.3% | 55.7% |
| Phosphorus, g | 56.8% | 58.7% | 85.2% | 86.8% |
| Potassium, g | 40.5% | 35.8% | 54.4% | 54.7% |
| Magnesium, g | 47.7% | 29.5% | 35.0% | 48.3% |
| Selenium, mg | 35.8% | 34.9% | 40.7% | 41.9% |
| Zinc, mg | 16.9% | 23.2% | 47.0% | 53.3% |
| Manganese, mg | 27.5% | 38.9% | 47.0% | 38.6% |
| Iron, mg | 149.3% | 108.3% | 156.8% | 173.1% |
| Copper, mg | 16.9% | 20.8% | 33.3% | 32.0% |
| Vitamin A, KIU | −19.2% | −19.7% | −16.3% | −15.6% |
| Vitamin E, IU | 283.2% | 281.3% | 297.7% | 301.0% |

TABLE 11

Percent differences in preferred pre-treatment concentrate intake of fatty acid components compared to control intake of concentrate fatty acid components

| | Preferred Diets | | | |
|---|---|---|---|---|
| | Canola Oil | | Fish Oil | |
| Item[a] | LSMF | MSHF | E:D1:1 | E:D2:1 |
| Total Fat, g | 52.2% | 95.4% | 89.6% | 88.7% |
| Total Unsaturated FA, g | 64.3% | 113.9% | 60.9% | 59.4% |
| Polyunsaturated FA, g | 27.3% | 52.9% | 50.8% | 50.0% |
| Monounsaturated FA, g | 152.8% | 260.1% | 85.1% | 82.1% |
| Saturated FA, g | 1.1% | 17.3% | 210.4% | 211.9% |
| Omega 3, g | 113.7% | 199.7% | 554.7% | 516.7% |
| Omega 6, g | 19.6% | 39.7% | 5.4% | 7.9% |
| Linoleic (18:2), g | 19.6% | 39.7% | 3.5% | 6.3% |
| α-Linolenic (18:3), g | 113.7% | 199.7% | 24.9% | 30.7% |
| Arachidic (20:0), g | 188.6% | 263.8% | 926.4% | 921.3% |
| Arachidonic (20:4), g | | | | |
| Eicosapentaenoic (20:5), g | | | | |
| Docosapentaenoic (22:5), g | 0.00% | 0.00% | 0.00% | 0.00% |
| Docosahexaenoic (22:6), g | | | | |
| Total EPA and DHA, g | | | | |

The total daily nutrient intake for a donor horse on the control diet and each of the preferred diets is shown below in Tables 12 and 13 on a dry matter basis.

TABLE 12

Total daily nutrient intakes for control and preferred pre-treatment diets on a dry matter basis

| | | Preferred Diets | | | |
|---|---|---|---|---|---|
| | Control | Canola Oil | | Fish Oil | |
| Item | Diet | LSMF | MSHF | E:D1:1 | E:D2:1 |
| DM, lbs | 27.74 | 29.22 | 29.16 | 29.54 | 29.62 |
| DM, kg | 12.61 | 13.28 | 13.25 | 13.43 | 13.46 |
| DE, Mcal | 31.75 | 33.22 | 34.08 | 34.60 | 34.91 |
| Total Fat, g | 270.89 | 351.84 | 417.15 | 408.43 | 407.01 |
| Ether Extract, g | 384.95 | 517.11 | 607.79 | 616.12 | 611.32 |
| Starch, g | 675.10 | 515.41 | 714.86 | 728.74 | 842.22 |
| Sugar, g | 1091.31 | 848.98 | 852.04 | 839.26 | 874.06 |
| Starch and Sugar, g | 1766.41 | 1364.39 | 1566.90 | 1568.00 | 1716.27 |
| Nonfibrous CHO, g | 3553.85 | 3782.23 | 3880.09 | 3953.27 | 4041.65 |
| Crude Protein, g | 2728.12 | 2557.49 | 2533.92 | 2583.56 | 2591.78 |
| Crude Protein:Energy ration, g/Mcal | 85.92 | 76.99 | 74.36 | 74.67 | 74.25 |
| Crude fiber, g | 2182.55 | 1476.07 | 1365.18 | 1378.26 | 1380.91 |
| Acid Detergent fiber, g | 3294.18 | 3446.86 | 3250.23 | 3246.09 | 3209.94 |
| Neutral Detergent fiber, g | 4421.31 | 4868.56 | 4729.95 | 4748.39 | 4688.21 |
| Ash, g | 1529.57 | 1651.50 | 1599.23 | 1622.37 | 1625.76 |
| Calcium, g | 206.92 | 229.73 | 228.92 | 239.58 | 239.77 |
| Phosphorus, g | 52.69 | 70.09 | 70.62 | 77.96 | 78.39 |
| CA:P ratio | 3.93:1 | 3.28:1 | 3.24:1 | 3.07:1 | 3.06:1 |
| Potassium, g | 307.47 | 70.09 | 70.62 | 375.53 | 375.66 |
| Magnesium, g | 38.12 | 45.57 | 43.03 | 43.80 | 45.65 |
| Selenium, mg | 3.85 | 4.56 | 4.54 | 4.66 | 4.68 |
| Zinc, mg | 1007.94 | 1336.15 | 1382.85 | 1560.87 | 1608.12 |
| Manganese, mg | 1338.34 | 1691.31 | 1781.41 | 1845.35 | 1778.89 |
| Iron, mg | 3053.34 | 4246.27 | 3915.56 | 4306.63 | 4438.18 |
| Copper, mg | 238.10 | 267.07 | 273.82 | 295.39 | 293.09 |
| Vitamin A, KIU | 335.30 | 321.58 | 321.25 | 323.45 | 323.90 |
| Vitamin E, IU | 1281.44 | 2593.03 | 2584.29 | 2660.36 | 2675.78 |

TABLE 13

Total daily fatty acid intakes for control and preferred pre-treatment diets on a dry matter basis

| | | Preferred Diets | | | |
|---|---|---|---|---|---|
| | Control | Canola Oil | | Fish Oil | |
| Item | Diet | LSMF | MSHF | E:D1:1 | E:D2:1 |
| Total Fat, g | 270.89 | 351.84 | 417.15 | 408.43 | 407.01 |
| Total Unsaturated FA, g | 197.10 | 276.93 | 337.55 | 272.86 | 271.04 |
| Polyunsaturated FA, g | 146.11 | 170.76 | 192.82 | 191.01 | 190.29 |
| Monounsaturated FA, g | 50.98 | 106.17 | 144.73 | 81.85 | 80.75 |
| Saturated FA, g | 73.79 | 74.91 | 79.60 | 135.57 | 135.98 |
| Omega 3, g | 49.84 | 59.73 | 65.87 | 91.20 | 88.49 |
| Omega 6, g | 95.11 | 111.02 | 126.95 | 99.82 | 101.80 |
| Omega 6:3 ratio | 1.91:1 | 1.86:1 | 1.93:1 | 1.09:1 | 1.15:1 |
| Linoleic (18:2), g | 95.11 | 111.02 | 126.95 | 98.33 | 100.54 |
| α-Linolenic (18:3), g | 49.84 | 59.73 | 65.87 | 53.40 | 53.81 |
| Arachidic (20:0), g | 1.83 | 2.68 | 3.01 | 5.91 | 5.89 |
| Arachidonic (20:4), g | 0.00 | 0.00 | 0.00 | 1.49 | 1.25 |
| Eicosapentaenoic (20:5), g | 0.00 | 0.00 | 0.00 | 19.66 | 19.36 |
| Docosapentaenoic (22:5), g | 0.00 | 0.00 | 0.00 | 0.00 | 0.00 |
| Docosahexaenoic (22:6), g | 0.00 | 0.00 | 0.00 | 17.68 | 14.83 |
| Total EPA and DHA, g | 0.00 | 0.00 | 0.00 | 37.34 | 34.19 |
| EPA:DHA ratio | 0.00 | 0.00 | 0.00 | 1.11:1 | 1.31:1 |

The percent difference in total daily nutrient intake for each of the preferred diets as compared to the control diet is shown below in Tables 14 and 15.

TABLE 14

Percent differences in preferred pre-treatment total daily nutrient intake components compared to control total daily nutrient intake components

| | Research | | | |
|---|---|---|---|---|
| | Canola Oil | | Fish Oil | |
| Item | LSMF | MSHF | E:D1:1 | E:D2:1 |
| DM, lbs | 5.3% | 5.1% | 6.5% | 6.7% |
| DM, kg | 5.3% | 5.1% | 6.5% | 6.7% |
| DE, Mcal | 4.6% | 7.3% | 9.0% | 9.9% |
| Total Fat, g | 29.9% | 54.0% | 50.8% | 50.3% |
| Ether Extract, g | 34.3% | 57.9% | 60.1% | 58.8% |
| Starch, g | −23.7% | 5.9% | 7.9% | 24.8% |
| Sugar, g | −22.2% | −21.9% | −23.1% | −19.9% |
| Starch and Sugar, g | −22.8% | −11.3% | −11.2% | −2.8% |
| Nonfibrous CHO, g | 6.4% | 9.2% | 11.2% | 13.7% |
| Crude Protein, g | −6.3% | −7.1% | −5.3% | −5.0% |
| Crude Protein:Energy ration, g/Mcal | −10.4% | −13.5% | −13.1% | −13.6% |
| Crude fiber, g | −32.4% | −37.5% | −36.9% | −36.7% |
| Acid Detergent fiber, g | 4.6% | −1.3% | −1.5% | −2.6% |
| Neutral Detergent fiber, g | 10.1% | 7.0% | 7.4% | 6.0% |
| Ash, g | 8.0% | 4.6% | 6.1% | 6.3% |
| Calcium, g | 11.0% | 10.6% | 15.8% | 15.9% |
| Phosphorus, g | 33.0% | 34.0% | 47.9% | 48.8% |
| CA:P ratio | | | | |
| Potassium, g | −77.2% | −77.0% | 22.1% | 22.2% |
| Magnesium, g | 19.6% | 12.9% | 14.9% | 19.8% |
| Selenium, mg | 18.3% | 17.8% | 20.8% | 21.5% |
| Zinc, mg | 32.6% | 37.2% | 54.9% | 59.5% |
| Manganese, mg | 26.4% | 33.1% | 37.9% | 32.9% |
| Iron, mg | 39.1% | 28.2% | 41.0% | 45.4% |
| Copper, mg | 12.2% | 15.0% | 24.1% | 23.1% |
| Vitamin A, KIU | −4.1% | −4.2% | −3.5% | −3.4% |
| Vitamin E, IU | 102.4% | 101.7% | 107.6% | 108.8% |

TABLE 15

Percent differences in preferred pre-treatment total daily fatty acid intake components compared to control total daily fatty intake components

| | Preferred Diets | | | |
|---|---|---|---|---|
| | Canola Oil | | Fish Oil | |
| Item | LSMF | MSHF | E:D1:1 | E:D2:1 |
| Total Fat, g | 29.9% | 54.0% | 50.8% | 50.3% |
| Total Unsaturated FA, g | 40.5% | 71.3% | 38.4% | 37.5% |
| Polyunsaturated FA, g | 16.9% | 32.0% | 30.7% | 30.2% |
| Monounsaturated FA, g | 108.2% | 183.9% | 60.5% | 58.4% |
| Saturated FA, g | 1.5% | 7.9% | 83.7% | 84.3% |
| Omega 3, g | 19.8% | 32.2% | 83.0% | 77.5% |
| Omega 6, g | 16.7% | 33.5% | 4.9% | 7.0% |
| Omega 6:3 ratio | | | | |
| Linoleic (18:2), g | 16.7% | 33.5% | 3.4% | 5.7% |
| α-Linolenic (18:3), g | 19.8% | 32.2% | 7.1% | 8.0% |
| Arachidic (20:0), g | 46.6% | 64.6% | 223.6% | 222.4% |
| Arachidonic (20:4), g | | | | |
| Eicosapentaenoic (20:5), g | | | | |
| Docosapentaenoic (22:5), g | 0.00% | 0.00% | 0.00% | 0.00% |
| Docosahexaenoic (22:6), g | | | | |
| Total EPA and DHA, g | | | | |
| EPA:DHA ratio | | | | |

The preferred donor diet comprises a typical feed concentrate (pellet form) and alfalfa hay combination that is appropriate for pre-treatment of a donor animal in accordance with the preferred embodiment of the present invention. The level of roughage (hay or pasture) in the diet is maximized since pasture and hay provides a favorable omega-6:omega-3 ratio which ranges from 0.3-1:5. Though it is important to maximize the roughage portion of the diet due to the favorable omega-3 ratio, the total content of fat in roughages is much lower than that in the concentrate. Therefore, on a weighted percentage of the total diet, it is more critical to insure that the carbohydrate and fat sources minimize excess omega-6 contributions in order to have the most influential impact from the immunonutrition component of the pre-treatment. The preferred feedstuff used in the concentrate are dehydrated alfalfa, distiller dried grain, yellow ground corn, wheat middlings, soybean hulls, molasses, canola oil, fish oil, algal sources of fatty acids, vitamin A, vitamin D, vitamin E, vitamin premix, trace minerals, salt, calcium carbonate, dicalcium phosphate, choline, selenium, ferrous sulfate, and magnesium oxide. In summary, the prescribed pre-treatment diet minimizes the amount of feedstuffs containing high proportions of omega-6 fatty acids and readily digestible sugars and starches (such as corn, corn oil, oats, and molasses) that promote inflammation.

A more preferred form of donor diet in accordance with the present invention maximizes the amount of feedstuffs containing fat, fiber, and more favorable ratios of omega-3:omega-6 fatty acids (such as milled flaxseed and flaxseed oil, linseed oil, canola oil, fish oil, soybean meal, and rice bran), as well as antioxidants that have a more favorable anti-inflammatory and pro-resolution profile. The most preferred donor diet includes a fish oil concentrate. The nutrient composition ranges for a preferred fish oil concentrate diet is presented on a dry matter basis in Tables 16 and 17 below. The fatty acid components are expressed as a percentage of total fat.

TABLE 16

Nutrient composition ranges for preferred pre-treatment concentrate diet on a dry matter basis

| Item | Min | Max | Range |
|---|---|---|---|
| DM | | | 88.00-93.00 |
| DE (Mcal/kg) | 2.55 | | 2.70-2.95 |
| (Mcal/lb) | 1.16 | | 1.23-1.34 |
| Total Fat (%) | 4.50 | | 6.00-12.00 |
| Starch (%) | | 18.00 | 11.00-16.00 |
| Sugar (%) | | 8.00 | 5.00-7.25 |
| Starch and Sugar (%) | | 26.00 | 16.00-23.25 |
| Nonfibrous CHO (%) | | 32.00 | 23.00-30.00 |
| Crude Protein (%) | 10.00 | 16.00 | 12.00-15.00 |
| Lysine (%) | 0.70 | | |
| Threonine (%) | 0.40 | | |
| Methionine (%) | 0.25 | | |
| Cysteine (%) | 0.20 | | |
| Crude fiber, max (%) | | 18.00 | 7.00-13.00 |
| Ash (%) | | | 8.00-12.00 |
| Calcium (%) | 0.80 | 1.80 | 1.00-1.75 |
| Phosphorus (%) | 0.60 | 1.30 | 0.75-1.25 |
| CA:P ratio | 1.25:1 | 3:01 | 2:01-2.5:1 |
| Potassium (%) | 1.00 | | 1.25-1.70 |
| Magnesium (%) | 0.30 | | 0.40-0.55 |
| Selenium (Se), mg/kg (ppm) | 0.60 | 0.80 | 0.60-0.70 |
| Zinc (Zn), mg/kg (ppm) | 200.00 | | 200.00-275.00 |
| Manganese, mg/kg (ppm) | 235.00 | | 245.00-280.00 |
| Iron, mg/kg (ppm) | 250.00 | | 275.00-550.00 |
| Vitamin A (KIU/lb), min | 5.00 | | 5.50-9.00 |
| Vitamin E (IU/lb), min | 90.00 | | 160.00-230.00 |
| Ascorbic Acid, mg/kg (ppm) | 40.00 | | 60.00-80.00 |

TABLE 17

Fatty acid composition ranges for preferred pre-treatment concentrate diet on a dry matter basis

| Item | Min | Max | Range |
|---|---|---|---|
| Total Fat, % | 4.50 | | 6.00-12.00 |
| Total Unsaturated FA, % | | | 60.00-70.00 |
| Polyunsaturated FA, % | | | 40.00-50.00 |
| Monounsaturated FA, % | | | 15.00-25.00 |
| Saturated FA, % | | | 22.00-30.00 |
| Omega 3, % | 12.00 | | 12.00-18.00 |
| Omega 6, % | | 35.00 | 20.00-30.00 |
| Omega 6:3 ratio | 1.5:1 | 8.0:1 | 6.0:1-1.5:1 |
| Linoleic (18:2), % | | 32.00 | 10.00-30.00 |
| α-Linolenic (18:3), % | 3.00 | | 4.00-10.00 |
| Arachidonic (20:4), % | | 1.00 | 0.40-0.75 |
| EPA:DHA ratio | 2:1 | 1:2 | 1:1-1.5:1 |
| Eicosapentaenoic (20:5), % | 6.00 | | 6.50-9.00 |
| Docosahexaenoic (22:6), % | | | 4.00-8.00 |
| Total EPA + DHA (mg/kg body wt) | 30.00 | | 40.00-60.00 |

In general, a preferred fish oil concentrate diet can be calculated for a horse of any size using values in Tables 18 and 19 below, representing daily nutrient intake attributable to the pellet component per 100 kg body weight dry matter basis, and Tables 20 and 21 representing total daily nutrient intake per 100 kg body weight dry matter basis.

TABLE 18

Daily nutrient intake ranges for preferred pre-treatment concentrate on a per 100 kg live body weight basis

| | Control | Preferred Fish Oil Concentrate Diet | |
|---|---|---|---|
| Item | Diet | Min | Max | Range |
| DM (% of body wt. in kg) | | | | 0.40-0.60 |
| DE (Mcal) | 1.15 | 1.20 | | 1.25-1.50 |
| Total Fat (g) | 17.80 | 30.00 | | 30.00-60.00 |

TABLE 18-continued

Daily nutrient intake ranges for preferred pre-treatment concentrate on a per 100 kg live body weight basis

|  | Control | Preferred Fish Oil Concentrate Diet | | |
|---|---|---|---|---|
| Item | Diet | Min | Max | Range |
| Starch (g) | 62.35 |  | 100.00 | 50.00-80.00 |
| Sugar (g) | 30.59 |  | 40.00 | 24.00-35.00 |
| Starch and Sugar (g) | 92.94 |  | 125.00 | 80.00-110.00 |
| Nonfibrous CHO (g) | 152.12 |  | 135.00 | 110.00-130.00 |
| Crude Protein (g) | 65.41 |  | 78.00 | 50.00-68.00 |
| Crude Protein:Energy ration, g/Mcal[a] | 56.93 | 37.00 | 60.00 | 40.00-55.00 |
| Lysine (g) |  | 3.50 |  |  |
| Threonine (g) |  | 2.00 |  |  |
| Methionine (g) |  | 1.25 |  |  |
| Cysteine (g) |  | 1.00 |  |  |
| Crude fiber (g) | 38.43 |  | 90.00 | 34.00-65.00 |
| Ash (g) | 31.92 |  |  | 40.00-60.00 |
| Calcium (g) | 5.57 | 4.00 | 9.00 | 5.00-8.50 |
| Phosphorus (g) | 3.25 | 2.50 | 6.25 | 3.00-8.50 |
| CA:P ratio | 1.71:1 | 1.25:1 | 3:1 | 2:1-2.5:1 |
| Potassium (g) | 5.06 | 5.00 |  | 6.00-8.00 |
| Magnesium (g) | 1.65 | 1.50 |  | 2.00-2.50 |
| Selenium (Se), mg | 0.24 | 0.25 | 0.37 | 0.30-0.35 |
| Zinc (mg) | 88.11 | 100.00 |  | 100.00-138.00 |
| Manganese, mg | 93.14 | 125.00 |  | 130.00-140.00 |
| Iron, mg | 95.08 | 125.00 |  | 150.00-250.00 |
| Vitamin A (KIU) | 7.51 | 6.06 |  | 6.00-8.00 |
| Vitamin E (IU) | 54.73 | 160.00 |  | 175.00-500.00 |
| Ascorbic Acid, mg |  | 25.00 |  | 65.00-900.00 |

[a]Total allotment of Crude Protein:Energy ratio in g/Mcal per day

TABLE 19

Daily fatty acid intake ranges for preferred pre-treatment concentrate on a per 100 kg live body weight basis

|  | Control | Preferred Fish Oil Concentrate Diet | | |
|---|---|---|---|---|
| Item | Diet | Min | Max | Range |
| Total Unsaturated FA (g) | 14.39 |  |  | 25.00-35.00 |
| Polyunsaturated FA (g) | 10.16 |  |  | 15.00-25.00 |
| Monounsaturated FA (g) | 4.23 |  |  | 7.50-15.00 |
| Saturated FA (g) | 3.41 |  |  | 10.50-15.00 |
| Omega 3 (g) | 0.84 | 4.75 |  | 5.25-8.50 |
| Omega 6 (g) | 9.32 |  | 18.00 | 10.00-16.00 |
| Omega 6:3 ratio | 11.09:1 | 1.5:1 | 8.0:1 | 6.0:1-1.7:1 |
| Linoleic (18:2), (g) | 9.32 |  | 16.00 | 9.00-13.00 |
| α-Linolenic (18:3), (g) | 0.84 | 1.50 |  | 2.00-5.00 |
| Arachidonic (20:4) | 0.05 |  | 0.50 | 0.15-0.40 |
| Eicosapentaenoic (20:5), (g) |  | 2.00 |  | 2.25-4.00 |
| Docosahexaenoic (22:6), (g) |  | 1.85 |  | 2.00-3.50 |
| Total EPA + DHA (mg/kg body wt) |  | 4.25 |  | 4.50-7.50 |

TABLE 20

Total daily nutrient intake ranges for preferred pre-treatment diet on a per 100 kg live body weight basis

|  | Original | Research | | |
|---|---|---|---|---|
| Item[[a]] | CBI | Min | Max | Range |
| DM (% of body wt. in kg) |  | 1.25 | 2.25 | 1.50-2.00 |
| DE (Mcal) | 3.74 | 3.60 |  | 3.80-4.25 |
| Total Fat (g) | 31.91 | 36.00 |  | 40.00-60.00 |
| Ether Extract (g) | 45.34 | 55.00 |  | 60.00-80.00 |
| Starch (g) | 79.52 |  | 100.00 | 60.00-90.00 |
| Sugar (g) | 128.54 |  | 110.00 | 80.00-100.00 |
| Starch and Sugar (g) | 208.06 |  | 200.00 | 140.00-190.00 |
| Nonfibrous CHO (g) | 418.59 |  | 480.00 | 400.00-470.00 |
| Crude Protein (g) | 321.33 | 220.00 | 305.00 | 240.00-300.00 |
| Crude Protein:Energy ration, g/Mcal[a] | 85.92 | 60.00 | 78.00 | 63.00-70.00 |
| Lysine (g) |  | 10.00 |  | 6.00-8.75 |
| Threonine (g) |  | 6.00 |  |  |
| Methionine (g) |  | 3.75 |  |  |
| Cysteine (g) |  | 3.00 |  |  |
| Crude fiber (g) | 257.07 |  | 180.00 | 140.00-170.00 |
| Ash (g) | 180.16 |  |  | 150.00-195.00 |
| Calcium (g) | 24.37 | 23.00 | 30.00 | 25.00-28.00 |
| Phosphorus (g) | 6.21 | 7.50 | 10.00 | 8.00-9.25 |
| CA:P ratio | 3.93:1 | 1.5:1 | 4:1 | 2:1-3:1 |
| Potassium (g) | 36.22 |  |  | 40.00-46.00 |
| Magnesium (g) | 4.49 |  |  | 5.00-7.00 |
| Selenium (Se), mg | 0.45 | 0.30 | 0.60 | 0.35-0.55 |
| Zinc (mg) | 118.72 |  | 185.00 | 120.00-175.00 |
| Manganese, mg | 157.64 |  | 200.00 | 140.00-185.00 |
| Iron, mg | 359.64 | 325.00 | 500.00 | 350.00-450.00 |
| Vitamin A (KIU) | 39.49 | 10.00 |  | 12.00-20.00 |
| Vitamin E (IU) | 150.94 | 200.00 |  | 225.00-325.00 |
| Ascorbic Acid, mg |  | 175.00 |  | 200.00-350.00 |

[a]Total allotment of Crude Protein:Energy ratio in g/Mcal per day

TABLE 21

Total daily fatty acid intake ranges for preferred pre-treatment diet on a per 100 kg live body weight basis

|  | Original | Research | | |
|---|---|---|---|---|
| Item[[a]] | CBI | Min | Max | Range |
| Total Fat (g) | 31.91 | 36.00 |  | 40.00-100.00 |
| Total Unsaturated FA (g) | 23.21 | 30.00 |  | 40.00-80.00 |
| Polyunsaturated FA (g) | 17.21 | 18.00 |  | 20.00-60.00 |
| Monounsaturated FA (g) | 6.01 |  |  | 8.00-18.00 |
| Saturated FA (g) | 8.69 |  |  | 10.50-15.00 |
| Omega 3 (g) | 5.87 | 7.25 |  | 7.50-12.00 |
| Omega 6 (g) | 11.20 |  | 16.00 | 10.00-14.00 |
| Omega 6:3 ratio | 1.91:1 |  | 6:1 | 1:1-6:1 |
| Linoleic (18:2), (g) | 11.20 |  | 16.00 | 10.00-14.00 |
| α-Linolenic (18:3), (g) | 5.87 | 7.00 |  | 7.25-12.00 |
| Arachidonic (20:4) | 0.00 |  | 0.25 | 0.12-0.20 |
| Eicosapentaenoic (20:5), (g) | 0.00 | 2.00 |  | 2.25-4.00 |
| Docosahexaenoic (22:6), (g) | 0.00 | 1.50 |  | 1.75-4.00 |
| Total EPA + DHA (mg/kg body wt) | 0.00 | 3.50 |  | 4.00-8.00 |

Alteration of chronic and exuberant inflammatory responses is more effectively manipulated by diet (i.e. addition of fat/omega-3 fatty acids) than by pharmacological means, as it restores balance and homeostasis versus targeting a single immune component or response. Due to redundancy of the immune system this approach also has longer lasting effects. Therefore, the preferred diets are also appropriate as direct feed diets to patient or at-risk horses as well. These altered diets work synergistically when fed concurrently with the local administration of the designer serum described below to resolve inflammation and other conditions and diseases.

The mean complete blood count values of horses fed with the control and preferred diets are shown below in Table 22.

TABLE 22

| Items | Reference | CONTROL | MSHF | LSMF | E:D1:1 | E:D2:1 | LSD[a] |
|---|---|---|---|---|---|---|---|
| WBC (×10³/uL) | 5.5-12.5 | 6.46 | 5.52 | 5.68 | 6.89 | 7.71 | 1.43 |
| RBC (×10⁶/uL) | 6.5-10.5 | 6.46 | 6.23 | 5.96 | 6.38 | 6.16 | 0.74 |
| HGB (g/dL) | 11-19 | 11.05 | 11.03 | 10.86 | 11.12 | 11.03 | 1.25 |
| HCT, % | 35-52 | 33.95 | 34.17 | 33.33 | 34.67 | 33.83 | 3.83 |
| MCV (fL) | 12.3-19.7 | 52.80 | 55.07 | 56.03 | 54.47 | 54.93 | 4.00 |
| MCH (pg) | 34-58 | 17.20 | 17.81 | 18.24 | 17.49 | 17.92 | 1.52 |
| MCHC (g/dL) | 31-37 | 32.55 | 32.37 | 32.60 | 32.07 | 32.72 | 0.87 |
| Platelet Ct (×103/uL) | 100-400 | 234.90 | 275.90 | 249.93 | 278.73 | 239.97 | 46.64 |
| ABS Neutrophils (/uL) | 2700-6700 | 4616.70 | 4165.60 | 3879.00 | 5378.90 | 5664.50 | 1257.8 |
| Neutrophils, % |  | 71.45 | 74.00 | 67.87 | 77.67 | 72.76 | 5.82 |
| Bands (/uL) |  | 0.00 | 0.00 | 0.00 | 0.00 | 0.00 | 0.00 |
| Lymphocytes (ABS /uL) | 1500-5000 | 1321.80 | 1025.00 | 1333.60 | 1029.40 | 1441.30 | 407.2 |
| Lymphocytes, % |  | 20.75 | 19.80 | 23.73 | 15.30 | 19.17 | 5.82 |
| Monocytes (ABS/uL) | 0-800 | 241.00 | 229.07 | 247.67 | 238.53 | 319.93 | 70.87 |
| Monocytes, % |  | 3.75 | 4.27 | 4.37 | 3.50 | 4.27 | 0.96 |
| Eosinophils (ABS/uL) | 0-925 | 269.15 | 93.10 | 221.87 | 243.43 | 291.90 | 114.26 |
| Eosinophils, % |  | 3.95 | 2.20 | 3.97 | 3.50 | 3.97 | 1.58 |
| Basophils (ABS/uL) | 0-170 | 6.35 | 3.77 | 1.23 | 0.00 | 0.00 | 8.49 |
| Basophils, % |  | 0.10 | 0.07 | 0.03 | 0.00 | 0.00 | 0.14 |

[a] Bolded Least Significant Difference value using $P < .05$ indicates a significant difference between diets.

The chemistry profile of serum produced from horses fed with the control and preferred diets are shown below in Table 23.

TABLE 23

| Items | Ref. | CONTROL | MSHF | LSMF | E:D1:1 | E:D2:1 | LSD[a] |
|---|---|---|---|---|---|---|---|
| Albumin (g/dl) | 1.9-3.9 | 2.91 | 2.91 | 2.85 | 2.72 | 2.69 | 0.23 |
| A/G ratio | .5-2.4 | 0.81 | 0.83 | 0.75 | 0.65 | 0.59 | 0.09 |
| Alkaline phosphatase (U/L) | 10-326 | 93.75 | 75.33 | 100.33 | 88.83 | 114.66 | 19.04 |
| Aspartate aminotransferase (U/L) | 180-570 | 219.40 | 197.77 | 226.2 | 182.97 | 220.55 | 35.91 |
| Blood urea nitrogen (mg/dl) | 10-25 | 19.05 | 17.27 | 17.80 | 16.97 | 16.90 | 1.78 |
| BUN/Creatine ratio | 5-21 | 19.85 | 18.77 | 18.17 | 17.47 | 16.57 | 2.81 |
| Calcium (mg/dl) | 10-13.7 | 10.76 | 10.94 | 10.94 | 10.88 | 10.96 | 0.38 |
| Chloride (mmol/L) | 95-110 | 97.50 | 98.23 | 97.57 | 99.03 | 99.43 | 1.33 |
| Creatine phosphokinase (U/L) | 20-500 | 199.65 | 194.70 | 217.33 | 181.47 | 178.41 | 90.64 |
| Cholesterol (mg/dl) | 70-150 | 75.15 | 91.5 | 84.20 | 82.37 | 84.35 | 9.32 |
| Creatinine (mg/dl) | 1.2-2.0 | 1.00 | 0.96 | 0.99 | 0.99 | 1.03 | 0.17 |
| Fibrinogen (mg/dl) | 76-400 | 168.35 | 179.60 | 178.37 | 182.83 | 197.45 | 20.12 |
| Gamma-glutamyltransferase (U/L) | 4.3-13.4 | 10.2 | 15.13 | 15.73 | 13.17 | 13.97 | 4.70 |
| Globulin (g/dl) | 2.6-5.6 | 3.67 | 3.62 | 3.81 | 4.25 | 4.72 | 0.39 |
| Glucose (mg/dl) | 70-120 | 81.40 | 79.87 | 71.00 | 72.07 | 70.31 | 6.31 |
| Lactate dehydrogenase | 150-450 | 332.20 | 328.23 | 369.73 | 357.43 | 369.69 | 91.6 |
| Phosphorus (mmol/L) | 2.0-5.6 | 3.44 | 3.61 | 3.51 | 3.74 | 3.74 | 0.42 |
| Potassium (mmol/L) | 3-5 | 3.79 | 3.99 | 4.14 | 3.96 | 4.08 | 0.23 |
| Sodium (mmol/L) | 30-146 | 133.40 | 138.00 | 136.53 | 133.67 | 131.72 | 1.16 |
| Sodium/Potassium ratio | 24-58 | 35.40 | 34.73 | 33.13 | 33.93 | 32.30 | 2.0 |
| T. Bilirum (mg/dl) | 0.1-2.5 | 0.39 | 0.38 | 0.35 | 0.36 | 0.39 | 0.07 |
| D. Bilirum (mg/dl) | 0.0-0.5 | 0.10 | 0.09 | 0.08 | 0.09 | 0.09 | 0.02 |
| Total protein (g/dl) | 5.2-8.0 | 6.58 | 6.54 | 6.66 | 6.97 | 7.41 | 0.34 |
| Triglycerides (mg/dl) | 25-120 | 21.20 | 23.33 | 18.70 | 16.40 | 15.76 | 4.49 |
| Iron (μg/dl) |  | 278.00 | 321.80 | 245.80 | 315.20 | 296.67 | 98.27 |
| Ferritin (ng/ml) [b] |  | 82.40 | 69.40 | 77.40 | 63.50 | 90.22 | 28.06 |
| TIBC (μg/dl) [c] |  | 436.00 | 505.89 | 437.20 | 496.60 | 469.78 | 53.41 |
| SAA[e] |  | 1.30 | 1.65 | 1.15 | 1.40 | 1.33 | 0.71 |

[a] Bolded Least Significant Difference value using $P < .05$ indicates a significant difference between diets.
[b] Biological availability of Fe
[c] Total Iron Binding Capacity The mean serum fatty acid profile of horses fed with the control and preferred diets are shown below in Table 24.

TABLE 24

| Items[b] | CONTR | MSHF | LSMF | E:D1:1 | E:D2:1 | LSD[a] |
|---|---|---|---|---|---|---|
| Total Fatty Acids | 1315.21 | 1883.09 | 1700.49 | 1485.33 | 1569.67 | 160.8 |
| Saturated Fatty Acids | 408.70 | 588.30 | 543.22 | 475.07 | 502.63 | 52.2 |
| Mono saturated Fatty Acids | 197.13 | 306.24 | 249.84 | 166.06 | 168.57 | 28.2 |
| Polyunsaturated Fatty Acids | 709.38 | 988.56 | 907.42 | 844.22 | 898.46 | 88.9 |
| Omega 3 Fatty Acids | 31.91 | 45.52 | 49.68 | 100.64 | 105.00 | 8.2 |

TABLE 24-continued

| Items[b] | CONTR | MSHF | LSMF | E:D1:1 | E:D2:1 | LSD[a] |
|---|---|---|---|---|---|---|
| Omega 6 Fatty Acids | 677.42 | 942.69 | 857.41 | 743.11 | 793.28 | 84.8 |
| Omega 9 Fatty Acids | 153.50 | 243.94 | 196.95 | 120.00 | 124.69 | 20.8 |
| Omega 6 to 3 ratio | 21.54 | 21.47 | 17.56 | 7.42 | 7.59 | 2.6 |
| Linoleic (18:2 n-6) | 654.26 | 913.10 | 829.07 | 694.35 | 747.56 | 82.3 |
| Gama-Linoenic (18:3 n-6) | 0.74 | 0.71 | 0.80 | 0.00 | 0.00 | 0.4 |
| Dihomo-GLA (20:3 n-6) | 3.83 | 4.55 | 4.76 | 6.19 | 6.88 | 0.7 |
| Arachidonic (20:4 n-6) | 14.95 | 18.26 | 17.19 | 39.42 | 34.38 | 2.6 |
| α-Linolenic (18:3) | 27.17 | 39.55 | 43.30 | 24.23 | 37.50 | 5.9 |
| Eicosapentaenoic (20:5 n-3) | 0.70 | 0.90 | 1.22 | 34.34 | 29.60 | 2.5 |
| Docosapentaenoic (22:5 n-3) | 2.69 | 3.08 | 2.89 | 9.82 | 9.54 | 0.8 |
| Docosahexaenoic (22:6 n-3) | 0.00 | 0.00 | 0.00 | 32.24 | 27.74 | 1.8 |

[a]Bolded Least Significant Difference value using $P < .05$ indicates a significant difference between diets
[b]Fatty acids are expressed in ug/ml of serum Pre-Treatment Vaccination The pre-treatment regimen may include an immunization protocol designed to enhance specific antibody spectrums in the donor's blood. Each donor is immunized for allergens, viral antigens, and/or bacterial antigens selected to enhance the profile of the blood product for purposes of preventing or mitigating a specific condition or disease. The two most common methods of vaccine administration are intranasal and intramuscular. An intranasal administration typically induces a local, effective mucosal immunity whereas an intramuscular administration induces a more systemic immune response. Alternative routes include: sublingual administration, which may reduce the risk of adverse reactions and stimulate both systemic and local immunity; or oral administration, which induces a systemic response via the gut-associated lymphoid tissue, mucosal-associated lymphoid tissue, and bronchial-associated lymphoid tissue. The effectiveness of the particular vaccine and the pathogen against which protection is desired generally dictate the preferred route of administration. Consideration may also be given to a combination of administration routes. For example, simultaneous or alternating administration of both intranasal and intramuscular vaccines.

In the preferred embodiment, the immunization protocol results in an increased production of antibodies capable of identifying or neutralizing allergens and antigens that would otherwise trigger an immune response resulting in inflammation. Example antibodies include isotypes of immunoglobulin (Ig) such as IgG (and sub-isotypes thereof), IgE, IgA, IgM, and IgT. For an equine serum intended to mitigate symptoms of IAD or RAO in horses, preferably immunizations against respiratory allergens known to induce IAD or RAO in horses are included in the pre-treatment. Examples include immunizations for various molds, such as Aspergillus fumigatus and Faenia rectivirgula, endotoxin, Beta-D-Glucan (found in molds, fungi, or pollens), dust (including hay, grain and stable bedding, mites debris/feces, vegetative material/plant debris), pollens (including grass, legume, tree, weed pollens), animal dander/epithelia, fungi, mites, and insects.

Immunizations against viral antigens may also be included in the regimen. Many of these vaccines are routinely given to horses via an intramuscular route of administration, such as Equine Herpes virus 1, 2, 4 and 5 and Equine Influenza virus. Some are not routinely given but recommended for pre-treatment in the preferred embodiment, including equine respiratory viral pathogens such as respiratory viruses such as equine rhinitis A and B. The regimen may also include immunizations for bacterial antigens such as Rhodococcus equi, Streptococcus equi, Escherichia coli and 7-way Clostridial which are more routinely administered to horses, as well as for other bacterial antigens known to be respiratory pathogens that contribute to IAD, including Streptococcus zooepidemicus, Streptococcus pneumoniae, Bordatella bronchiseptica, Fusobacterium, Actinobacillus spp, Pasteurella spp, and Mycoplasma.

The vaccination/immunization regimen for the majority of the allergens preferably includes vaccinations for endotoxin, Aspergillus fumigatus, Faenia rectivirgula, mite extracts (debris/feces), hay dust, grain dust, and other pollens or allergens, preferably at least endotoxin, Aspergillus fumigatus and Faenia rectivirgula. These vaccinations are handled in two different sets: Set 1 (grass, legume, tree, weed pollens, and animal dander/epithelia); and Set 2 (molds, mites, insects, dust). The preferred allergen dosing schedule decreases in frequency but increases in concentration of antigen over time until a maintenance dose and time schedule are reached. For example, a low dose may be given every 2-3 days for four doses, followed by every 7-10 days for four doses, followed by every 14 days for four doses, then to every 21-30 days for 3-4 doses, then to maintenance of every three months. The content and concentration of the antigens starts out weak and gets stronger as time goes on until the maintenance levels are reached.

Vaccines for endotoxin and for the bacterial and viral vaccines such as Herpes Virus 2 & 5, Equine Rhinitis A & B, Streptococcus zooepidemicus, Streptococcus pneumoniae, Staphylococcus pneumoniae, Actinobacillus, Pasteurellaceae, Bordatella bronchiseptica, Fusobacterium, and Mycoplasma preferably follow an industry accepted standard protocol including 2 initial intramuscular vaccines given 4 weeks apart. This would then be followed by a hyperimmunization regime of an intramuscular vaccine every 3rd month.

Additional Pre-Treatment

In addition to the diet and immunization regimen described above, a donor horse may also be pre-treated with immunostimulants, aspirin, probiotics, oral allergens and antibodies, or other medicants. In another example, adding an aspirin supplement in conjunction with the omega-3 supplement produces a more stable stereoisomer of an omega-3 fatty acid metabolite. This metabolite is a resolvin that assists in modulating immune response and resists rapid breakdown in the lungs. In addition, an oral IgG product may be top-dressed on the feed daily for 30 days prior to blood collection.

Non-specific immunostimulants enhance immune system cell function (for example, phagocytosis and oxidative burst of macrophages and neutrophils) and specific antibody production. They also influence other immunomodulators to aid in the recovery from minor chronic bacterial infections and viruses that interfere with the respiratory and reproductive systems. One example is Zylexis (parapox ovis virus available through Pfizer), which activates immune cells and stimulates phagocytosis and expression of cytokines, the messenger proteins that stimulate production of interferon and immune cells. Preferred dosing is a 2 ml injection on days 0, 2, and 9 prior to stress inducing situations. A second example is EqStim (*Propionibacterium acnes* available through Neogen), which increases INF-gamma (type 1 cytokine) and NK-lysin gene expression (anti-microbial peptide) in peripheral blood mononuclear cells. Preferred dosing is 1 ml IV/250 lbs body weight on days 0, 3 or 4, and 7 and weekly thereafter as needed. A third example is Equimune (inactivated *Mycobacterium bovis; bacillus* Calmette-Guerin available through Bioniche). Preferred dosing is 1.5 ml IV as an initial dose and repeated in 1-3 weeks. A fourth example is Settle (Mycobacterial cell wall extract). Preferred dosing is 1.5 ml IV during the estrus cycle. A fifth example is an oral administration of low-dose interferon alpha that lowers nucleated cell counts in the bronchoalveolar lavage fluid of horses with inflammatory airway disease and converts the differential cell analysis to a non-inflammatory cytology. Interferon-gamma (INF-γ) and Granulocyte Colony Stimulating Factor (G-CSF) could also be used to enhance various components in the preferred serum product.

Blood Collection and Processing

The pre-treatment regimen is consistently implemented with respect to the members of the donor group to ensure that the blood levels of the desired anti-inflammatory profile components are sufficiently high. Preferably, the donors are pre-treated for at least thirty days, more preferably, the donors are pre-treated for at least 60 days, and most preferably, the donors are pre-treated for at least 90 days before blood collection. After the donors are pre-treated for the prescribed period of time, blood can be collected for production of the serum having an enhanced profile. The donor animals then continue on the pre-treatment diet and supplements, as well as with maintenance level vaccinations as described herein, for as long as they remain donor animals for the blood product.

The blood may be collected from the donors in any manner deemed suitable and known in the art for that particular species of donor. An example of a suitable method of collecting whole blood from livestock, and specifically horses, is fully described in U.S. Pat. No. 5,548,066, which is incorporated herein by reference. In collecting the whole blood, it is preferable to use sterile collection vessels made of glass. The benefits of glass collection vessels include clot initiation, ease of cleaning and sterilization, and lack of leaching from plastic. In a more preferred embodiment, medical grade borosilicate glass and incubation vessels are used. Other surfaces such as medical-grade glass blood collection tubes, borosilicate glass beads, chromium sulfate, gels glass wool, granulated materials, and particles of styrene can stimulate white blood cells and platelets (specifically neutrophils and macrophages) and may be used to produce anti-inflammatory cytokines and healing growth factors.

After the blood is collected, it is processed to produce the desired blood product. In the preferred embodiment, the blood product is a concentrated serum. The preferred extraction process includes the steps of allowing the blood to clot, pressing the clotted blood, separating the blood to isolate the serum, concentrating the serum (preferably by a factor of 1.5-5×, more preferably 2-4×, and most preferably 4×), and sterilizing the serum. Such extraction processes are known in the art. A preferred extraction process is fully described in U.S. Pat. No. 5,548,066, which is incorporated herein by reference. In a preferred embodiment, the serum is isolated from the clotted blood 12-48 hours from collection. In a more preferred embodiment, the blood is allowed to clot for a minimum of 24 hours. It is believed that certain components, such as growth factors are time-sensitive with regard to formation, synthesis, and secretion. Specifically, it has been found that growth-factors of an anti-inflammatory nature are present in higher concentrations after the first 24-hour period post-collection. This collection-to-isolation/harvest time-frame may be altered to selectively harvest other growth factors, such as pro-inflammatory growth factors and cytokines, at peak times and depending on the desired component profile of the final concentrated serum. In addition, clotting stimulants may be added to the collected blood to speed-up the formation, synthesis, and secretion of certain factors. For example, Bovine Thrombin (0.1-1 iu/ml) or erTNF (1-100 ng/ml) may be added.

The temperature of the blood during clot incubation can also be manipulated to increase the presence of certain anti-inflammatory and other desirable components. In a preferred embodiment, the blood is kept at ambient/room temperature (20-25° C.) for 15-60 minutes, followed by transfer to a warm room (30-35° C.) for 3-4 hours. The blood is then transferred to a cool room (2-8° C.) for 24-48 hours. The incubation temperature may be modified in other ways as well (i.e. 37° C. for 24 hours) in order to optimize the level of desired growth factors. In a more preferred embodiments, the cool room incubation is done in a borosilicate glass container. Glass vials containing lead beads are preferably dropped in at 6-24 hours after collection, and most preferably dropped in at 24 hours post-collection.

Serum Composition

The resulting separated serum includes components that assist a patient's immune system in avoiding or perpetuating exuberant inflammation such as antibodies, growth factors, immune system mediators, immune system stimulants, and/or other components. In a preferred embodiment, the separated serum has an enhanced profile characterized by one or more of the following components:

a. Specific antibodies for major allergenic and antigenic factors associated with airway inflammation. Antibodies, including IgG sub-isotypes, IgA, IgE, IgM, and IgT, primarily function as inflammation resolution factors. Airborne dusts in equine stables contains a range of organic and inorganic allergens which include but are not limited to bacteria, viruses, hay molds and fungi (i.e. *Aspergillus fumigatus* and *Faenia rectivirgula*) forage and dust mite debris and their feces, plant/vegetative material, endotoxins, β-D-Glucans, inorganic dusts, *Lichtheimia corymbifera, Eurotium emstelodami*, sheep wool epithelium, mixed feathers, insect secretions (mosquito, blackfly, other flies, ants), weed dust, tree pollens, individual molds, rusts, and grass-type hays, red clover, alfalfa pollen, corn pollen, grain mill dust, mustard, yellow dock, grass smut mix, grain smut mix, oat stem rust, wheat stem rust, and mite dust. Components of stable dust are somewhat variable depending on the area with the exception of a few primary components that consistently induce inflammation. Antibodies target specific inflammatory molecules, their receptors, or components of signaling pathways. Horses susceptible to airway disease can utilize these local antibodies in a passive manner to combat deficiencies of these necessary antibodies and neutralize the offending allergens and infectious antigens to prevent continual induction of inflammation. The presence of such antibodies mitigates or prevents exuberant inflammatory immune responses. Additional antibodies against infectious agents (bacterial/viruses) that horses are continually exposed to include EHV-1,4,5, EIV, *Streptococcus pneumonia, Streptococcus zooepidemicus, Streptococcus equi, Actinobacillus* spp, *Mycoplasma, Bordatella bronchiseptica, Pasteurella* spp, and Equine Rhinitis A & B, are very important. These antibodies decrease the induction of inflammatory mediators (i.e. TNF-α, IL-1β), interfere with inflammatory cascades, repress inflammation, and mediate allergic airway inflammation by preventing the induction of inflammation in continual presence of allergens. In general, allergen and pathogen antibodies target specific inflammatory molecules, their receptors, or components of signaling pathways. The pre-treatment hyperimmunization regimen maximizes the level of desired antibodies in the preferred serum product. Omega-3 Fatty Acids and hyperimmunization regimes will increase immunoglobulins and possibly specific immunoglobulin subtypes, such as IgGb as well as the IgGb:IgGa ratio for a more protective response. IgGb (IgG4 and IgG7) are the most important subtypes with subtypes 1 (IgGa), 4, and 7 having the highest level of antigen binding. IgGs 1, 4, and 7 possess the ability to activate macrophages and are able to fix complement, which are important and necessary functions. Vaccines that produce IgG subtypes 1, 3, 4, and 7, are the most protective in terms of antigen neutralization. Recent studies have shown an association between heaves and resistance to parasitic infections, so antibodies to parasites may also be beneficial and consideration should be given to immunization of donors with such antigens. The concentration of the final serum, as well as selection of the donor horses, also increases the array of antibodies present.

b. Anti-inflammatory factors that reduce and signal the resolution of inflammation, such as DHA, EPA, anti-inflammatory eicosanoids from the cyclooxygenase (COX) and lipoxygenase (LOX) pathways, other cytokine and chemokine chemical mediators, and resolution mediators including lipoxins, resolvins, protectins, and maresins, enhanced in the serum by pre-treatment dietary manipulation of donor horses by direct omega-3 fatty acid supplementation. Omega-3 Fatty Acid supplementation also results in decreased cellular adhesion molecules (CAM; decreased chemotaxis and migration), decreased NF-KB activity, oxidative stress, mucus production, fibrosis, lung damage (due to decreased recruitment, infiltration, and activation of neutrophils), bronchoconstriction, and improved lung function.

c. Anti-inflammatory cytokines and mediators maximized in the serum product whose function is to reduce the level of exuberant inflammation (for example, interleukin-10 (IL-10), IL-1Ra, IL-4, 6, 11, 13, TGF-beta). This is accomplished through the pre-treatment diet, selection of the donor horses, a large donor herd, the time between blood collection and serum harvest (a time period of 24 hours) minimizes the level of pro-inflammatory cytokines, and the concentration process.

d. Pro-inflammatory cytokines (INF-γ, TNF-α, IL-1β, 2, 3, 4, 5, 6, 7, 8, 9, 10, 11, 12, 13, 17, 23, and TGF-b) and chemokines (GCSF and GM-CSF, CXCL-8, CCL2, CCL3, CCL11, CXCL10, CCL5, regulated on activation, Normal T Cell Expressed and Secreted (RANTES), CXCL2, MIP-1,2 (macrophage inflammatory protein), MCP-2 (monocyte chemoattractant protein), and HIF (hypoxia induced factor)), as well as pro-inflammatory NFKB mediators minimized in the preferred serum product. This is accomplished through the pre-treatment diet, selection of the donor horses, a large donor herd, the time between blood collection and serum harvest (a time period of 24 hours) minimizes the level of pro-inflammatory cytokines, and the concentration process.

e. Antioxidants (including but not limited to Vitamin E, Vitamin C, selenium, astaxanthin, coenzyme Q10, superoxide dismutase, melatonin, black tea, cranberries, elderberry, orange peel, ginger, echinacea, yucca, bioflavinoids, N-acetyl cysteine, grape seed extract, milk thistle, resveratol, beta-carotene, alpha-lipoic acid, methyl sulphonyl methane, copper, and zinc) which protect tissue from free radical activity during metabolism, exercise, and inflammation. Antioxidants primarily function as inflammation resolution factors or agents and their presence in the serum is affected by the pre-treatment diet, selection of young, healthy horses with no evidence of systemic inflammation, a large donor herd, harvesting the serum at 24 hours, and concentration of the final serum product.

f. Growth factors which primarily serve a healing function. When whole blood clots naturally, the α-granules within the platelets release growth factors including but not limited to Insulin-like Growth Factor (ILGF), Fibroblast Growth Factor (FGF), Platelet Derived Growth Factor (PDGF), Transforming Growth Factor-Beta (TGF-B), Vascular Endothelial Growth Factor (VEGF), Hepatocyte Growth Factor (HGF), and Epidermal Growth Factor (EGF) that contribute to coordinated repair in damaged tissue or maintain tissue integrity without excessive fibrosis or perpetuation of inflammation and tissue destruction. The downside is that in some situations, growth factors may perpetuate remodeling and fibrosis Growth factors are immunomodulators and some of the indirect modulatory actions include increased IL-10 secretion by macrophages, TGF-β-associated decreased Natural Killer (NK) cells, inhibition of T cell proliferation, provision of homeostatic balance, downregulation of pro-inflammatory cytokines and upregulation of anti-inflammatory cytokines (IL-10 and IL-1RA in BALF), decreased goblet cell metaplasia and mucus hypersecretion, decreased airway remodeling, and increased numbers and response of T reg cells. Some factors have opposing positive and negative function such as TGF-β, where this growth factor is a key mediator in pulmonary fibrosis and airway remodeling and has been shown to increase airway hyperresponsiveness (AHR), but has anti-inflammatory properties. The presence of these factors, and growth factors in particular, in the final serum is enhanced or minimized by time between blood collection and serum harvest and the final concentration of the serum.

g. MicroRNA-mediated interference or blockade has been identified as a novel mechanism that may explain the mechanism of action of some anti-inflammatory therapies. MicroRNA expression is regulated by multiple factors including growth factors, inflammatory agents, anti-inflammatory mediators, mechanical forces, hypoxia, and others. It regulates protein expression at the gene or translational level and impacts the production and release of pro-inflammatory mediators (i.e. cytokines and others), inflammatory signaling pathways (NF-KB and Toll Like Receptor (TLR)), apoptosis, and remodeling. For example, TLR signaling and microRNAs have been linked and coupling of these pathways form regulatory signaling of innate immune responses which leads to activation of inflammatory pathways and promotion of adaptive immune responses. Data suggests that not one, but an interplay of multiple microRNAs are likely to regulate inflammation and its sequellae. On the other hand, a single microRNA can target hundreds of mRNAs and modulate protein output from their respective genes. Another illustration may include a scenario where LPS-induced inflammation may increase expression of microRNA-155, which upregulates the pro-inflammatory cytokine IL-8 thus perpetuating inflammation. In contrast, providing increased amounts of IL-10, which is an anti-inflammatory cytokine that is present in our serum will inhibit lipopolysaccharide/endotoxin (LPS)-induced microRNA-155 expression and reduce inflammation towards resolution.

h. Neutrophils present in large numbers in the airways of horses may contribute to the disease through the release of several inflammatory mediators and are recruited 3-5 hours following exposure to stable dust, but damage is reversible with exposure removal. Delayed spontaneous apoptosis, high levels of activation leading to increased elastase and other damaging mediator production, increased oxygen metabolite release, and increased LTβ4 and MMP-9 production and release are detrimental consequences. Release of IL-1β and TNF-α have been reported to contribute to sustained inflammation as well as NF-KB activity. Along the same lines, macrophage density and increased activation occur causing increased IL-1β, TNF-α, IL-8, and MIP-2 following stable dust challenge. Mold antigens favor cellular activation of macrophages independent of clinical diagnosis. Anti-inflammatory therapies (including fish oil) may trigger phenotype switch of macrophages and/or neutrophils in BALF which can drive ongoing inflammation down the pro-resolution pathway. Molecular switches may exist that selectively induce activation and deactivation of regulatory pathways that manifest in anti-inflammatory activity. The phenotypic switch from M1 (classically activated macrophages) to rM (resolution phase macrophages) and the appearance of resolution phase lymphocytes are the cardinal signs of resolution. In terms of neutrophils, anti-inflammatory therapies may restore apoptosis and removal of inactivated neutrophils from the lung by resolution phase macrophages. This rids the environment of prolonged neutrophil activity and release of mediators that serve to cause lung damage and destruction from persistence of antigen. Neutrophils switch mediators from leukotrienes to lipoxins (present in serum product) that serve as anti-fibrotic agents and potent stop signals for neutrophil infiltration and downregulate cytokine and reactive oxygen species release, and promote nonphlogistic recruitment of macrophages that are stimulated to remove apoptotic neutrophils. This phenotype switching phenomenon has the ability to turn off inflammation and restore homeostasis. No single agent triggers all cardinal signs of resolution though RvE1 and Lipoxin A4 followed by dexamethasone demonstrate the most resolution possible properties.

i. Iron-binding proteins (Transferrin, Ferrotin, Lactoferrin, Ferroportin, and Ceruloplasmin) which are potent antioxidants and act primarily as immunomudulators that control the level of free iron and reduce oxidative damage. Ceruloplasmin is also a potent antioxidant that permits incorporation of iron into transferrin without the formation of toxic iron products, as well as aids in the control of membrane lipid oxidation. Selection of young, healthy horses, with no systemic inflammatory conditions, a large donor herd, and the concentration process enhances the presence of these proteins in the serum.

j. Proteins that prevent pro-inflammatory cytokines from binding tissue receptors and causing damage (for example, IL-1 Receptor Antagonist Protein (IRAP), which prevents IL-1 from binding IL-1 tissue receptors).

k. Anti-cytokine antibodies that neutralize pro-inflammatory cytokines (for example, neutralizing antibodies for TNF-alpha and IL-1).

l. Soluble cytokine receptors that regulate inflammation and immune system pathways by functioning as pro-inflammatory cytokine inhibitors (for example, Tumor Necrosis Factor-alpha (TNF-alpha), interleukin-6 (IL-6), interleukin-1 Beta (IL-1B), interleukin-8 (IL-8), and interleukin-18 (IL-18)).

m. Annexin-1A (Lipocortin) which is an immunomodulator. It inhibits phospholipase A2 activity, which is necessary for the production of potent inflammatory mediators such as prostaglandins and leukotrienes, and can reduce superoxide, free radicals, and neutrophil accumulation, as well as modulating neutrophil adhesion and migration. On the other hand, Lipocortin can also induce instead of inhibit these processes if necessary. Lipocortin, therefore serves as a general regulator and modulator of neutrophil recruitment. The presence of this component is enhanced in the final serum product by a large donor herd and final serum concentration.

n. Tissue inhibitors of metalloproteinases (i.e. TIMP-1) which are peptidase inhibitors that inhibit matrix metalloproteinases (MMPs), especially 2 & 9 that have been implicated with respiratory inflammation, and act as immunomodulators.

o. Proteins such as Surfactant proteins A and D which are part of the innate pulmonary defense mechanism and primarily function as immunomodulators by suppressing allergic airway response, attenuating airway hyper-responsiveness (bronchoconstriction), increase in airway compliance (increased airway opening), inhibiting the production of pro-inflammatory cytokines, and promoting clearance of excess mucus by the mucociliary apparatus as well as pathogens and allergens. They facilitate phagocytosis by alveolar macrophages, provide antimicrobial properties, decrease surface tension and therefore collapse of alveoli, and function as anti-inflammatory chemicals and antioxidants. The enhanced presence of these components in the serum is due to selection of the donor horses and the size of the donor herd.

p. Pro-inflammatory mediators such as TNF-α may augment increased mucus production and accumulation via the MUCSAC gene found in equine epithelial cells which leads to airway plugging and obstruction. Reducing pro-inflammatory mediators such as TNF-α with anti-inflammatory therapy may decrease excess mucus production.

q. Proteins such as Clara cell secretory proteins which are immunomodulators and function to protect tissues by decreasing inflammation, resisting the development of pulmonary fibrosis, inhibiting phosphodiesterase A2 (thereby decreasing the production of pro-inflammatory mediators such as leukotrienes and prostaglandins), increasing phagocytic function, and decreasing oxidative activity of neutrophils. The presence of these proteins in the serum is enhanced by concentrating the serum and the size of the donor herd.

r. Altered lymphokines that stimulate phagocytosis and oxidative burst of alveolar macrophages and neutrophils to clear debris and antigens due to the altered lymphocyte populations (i.e. CD4, CD8, Th1, and Th2) in the circulating blood as a result of dietary pre-treatment of the donor herd.

s. Complement components (C3, C3a, and C3b) that serve as immunomodulators. They are opsonins for pathogens or allergens that aid in the phagocytosis, destruction (cytolysis), and elimination of foreign proteins from the respiratory tract. Complement components also enhance chemotaxis of neutrophils. The presence of these compliment components and inhibitors are enhanced in the serum by the selection of young, healthy horses free of systemic inflammatory conditions, the concentration process, and a large donor herd.

t. Panproteinase inhibitors, such as Alpha-2-Macroglobulin and Alpha-1-Antitrypsin that are classified as anti-proteases and generally function as immunomodulators. These binding proteins attach to inflammatory cytokines and aid in humoral defense and clearance. They are also helpful in inhibiting virus replication and combating endotoxins by preventing excessive tissue damage. They prevent lung function decline in chronic lung disease. The presence of these components in the final serum is primarily affected by the size of the donor herd and final product concentration.

u. Various constituents may influence Regulatory T cells/lymphocytes which control inflammation resolution.

v. Anti-inflammatory therapy may impact some portion of the Th1, Th2, and/or Th17 response pathways.

w. NF-KB activity and TLR2 and 4 expression may be important pathways that could be influenced by anti-inflammatory therapy. Increased TLR4 expression leads to exaggeration of innate immune response and NF-KB activity which correlates to parameters of lung function and increased intracellular adhesion molecule (ICAM-1) expression, and facilitation of neutrophil recruitment.

There are so many proteins/components in serum that there are likely mechanisms of action that have yet to be discovered that are beneficial and contribute to the multifactorial response to therapy. Also, it may be that slightly different formulations (i.e. harvest time and incubation conditions) for different body systems (i.e. certain growth factors and/or levels might work better at maximized levels for conditions such as osteoarthritis where cartilage defect healing is key versus pulmonary inflammation where excessive fibrosis would be detrimental).

Method of Using Serum Product

In the preferred embodiment, the concentrated designer serum with the enhanced profile described above is used to prophylactically treat patient horses susceptible to IAD or mitigate the established inflammation in horses with IAD or RAO. In addition to having a local effect on lung inflammation, the serum product may also help reduce systemic inflammation that may be present during acute exacerbation and persist even when the primary inflammatory disease is in remission.

The serum is preferably delivered to a localized area, namely the lungs. The serum may be administered in an intranasal, intratracheal, or nebulized fashion as is known in the art. Examples of these delivery methods are disclosed in U.S. Pat. No. 6,770,278, which is incorporated herein by reference. Preferably, the dose is about 1 mL to about 80 mL of an approximately 0.12 gm/mL IgG serum. The preferred dosing regimen includes a loading dose once every 24 hours for a total of five treatments, followed by weekly treatments. Additional doses may be given between 24 and 48 hours prior to competition, strenuous exercise, or long-distance transport.

Concentrated serums with alternative enhanced profiles may be used to prevent or mitigate other diseases and conditions, including but not limited to other inflammatory conditions or disease such as those previously described. The serum may be administered orally or locally/topically, which may necessitate an injection (i.e., intratracheal or intratraarticular), a transnasal catheter, or endoscopically-guided intrabronchial spray as appropriate. It may also be administered via intramuscular or intravenous injection in certain situations. However, this would require careful consideration due to the possibility of anaphylactic reaction to foreign proteins. An example of where oral administration would be appropriate is to a neonate to boost immunization. Alternatively, the serum product could be encapsulated into micro spheres for local administration by nebulization to optimize a sustained release of the product and decrease the number of doses required.

Anti-inflammatory activity and immunizing immunotherapy are mediated by the Ig E and/or IgG and IgA subclasses when administered orally. Immunoglobulin specificity may be possible, but it also seems effective in the absence of the allergen in the patient. Passive immunity via oral antigen-specific IgG reduces/prevents allergic airway inflammation manifestation in later life, in newborns nursing, and helps by oral administration to lactating females which transfer protection to the offspring. An intraarticular injection may be used to treat an arthritic joint. Topical or intraocular injections can be used for ophthalmic indications such as refractory corneal ulcers or recurrent uveitis. Intranasal or intratracheal injections as well as nebulization or oral doses may be used for passive protection against airway allergens or infectious agents. The serum product may also be applied locally to the uterus (intrauterine) to address reproductive disorders, maintain pregnancy, or promote conception. In addition, the serum may be administered topically to a wound or to the internal surface of the abdomen (topically or via intraperitoneal injection) before, during, or after colic surgery. Applications are not limited to the equine species and principles and concepts may be utilized for similar conditions in other species, including companion animals and livestock.

EXAMPLE 1

Control Blood Product

Processes for harvesting blood from a donor animal group and producing serum products therefrom are known in the prior art. A control donor group and method of production consistent with these prior art processes is set forth below for comparison to the method of the present invention:

a. The control donor group consists of at least one hundred horses exhibiting generally good health (but not pre-screened or tested for any inflammatory diseases or conditions). A majority of the horses are mature and the horses originate from at least five different geographic regions so as to contribute immunity to pathogens of various regions of the country.

b. The control donor group is hyperimmunized with the following vaccinations: Equine Influenza Virus, Equine Herpes Virus (1 and 4), *Rhodococcus equi, Streptococcus equi, Escherichia coli*, and 7-way Clostridial vaccine (bacterial antigen). For each, 2 initial intramuscular vaccines given 4 weeks apart followed by hyperimmunization regime of intramuscular vaccine every 3rd month.

c. Representative diet for control group is set forth in Table 2 above. The control diet is characterized by a high protein:energy ratio with relatively high levels of starches/sugars, relatively low levels of fat for an energy source and no EPA or DHA sources of Omega-3 fats. No additional nutrients, supplements or medicants are added to the control diet as a matter of course.

d. The blood collected from the donor animals is pooled and processed to produce a serum in accordance with the process described in U.S. Pat. No. 5,548,066.

EXAMPLE 2

Pre-Treatment Donor Selection

A method of producing a blood product, preferably a serum product, in accordance with the present invention includes pre-treating a plurality of donor animals in a manner to increase blood levels of one or more factors associated with healthy immune response mechanisms. In this example, at least 50 donor animals, and most preferably at least 100 donor animals are pre-treated, where a majority of the donor animals are gelding draft horses. The donor animals originate from at least two different geographic areas and more preferably at least five different geographic areas, each being at least 100 miles apart.

In one embodiment of this method, all of the donor animals are horses and a majority of the donor animals have been screened and found to be substantially free of one or more of the following: A & Q antibodies, Equine Infectious Anemia (EIA), Equine Piroplasmosis (*Babesia theilleria* and *caballi*), Brucellosis abortus, Dourine (*Trypanosoma equiperdum*), Glanders (*Burkholderia mallei*), and/or Equine Viral Arteritis (AVA). In a preferred embodiment, a majority of the donor animals have been screened and found to be substantially free of all of the following: A & Q antibodies, Equine Infectious Anemia (EIA), Equine Piroplasmosis (*Babesia theilleria* and *caballi*), Brucellosis abortus, Dourine (*Trypanosoma equiperdum*), Glanders (*Burkholderia mallei*), and/or Equine Viral Arteritis (AVA).

In another embodiment, the donor horses are mature and also do not exhibit symptoms of excessive inflammation. Most preferably, the donor horses do not exhibit significant evidence of osteoarthritis, Insulin Resistance, Equine Metabolic Syndrome, obesity, Cushings Disease, Equine Polysaccharide Storage Myopathy, Recurrent Airway Obstruction, muscle inflammation, Recurrent Rhabdomyolysis, laminitis, and hoof inflammation or other conditions or diseases associated with systemic inflammatory conditions. If the donor animals are diagnosed with an illness, disease, or condition after initiation of pre-treatment, they are removed from the donor herd.

EXAMPLE 3

Pre-Treatment Vaccination

A method of producing a blood product, preferably a serum product, in accordance with the present invention includes pre-treating at least one donor animal with an immunization regimen in a manner to increase blood levels of one or more factors associated with healthy immune response mechanisms. In this example, the donor animals are horses and are vaccinated against one or more bacterial antigens known to be respiratory pathogens that contribute to IAD. Specifically, the donor animals are vaccinated against one or more bacterial antigens selected from the group of *Streptococcus zooepidemicus*, *Streptococcus pneumoniae*, *Bordatella bronchiseptica*, *Fusobacterium*, *Actinobacillus* spp, *Pasteurella* spp, and *Mycoplasma*. The donor animals may also be vaccinated with the vaccinations set forth above under Example 1 given to the control donor group.

In one embodiment, the donor animals are also vaccinated against one or more equine respiratory viral pathogens. Preferably, the donor animals are vaccinated against equine rhinitis A and B, and most preferably against equine herpes virus 2 and 5 and equine rhinitis A and B. The donor animals may additionally be vaccinated against the bacterial antigens selected from the group consisting of *Streptococcus equi* and *Rhodococcus equi* and against the viral antigens selected from the group Equine Herpes Virus (EHV; 1,2,4,5) and Equine Influenza Virus (EIV).

In another embodiment, the donor animals are also vaccinated against one or more respiratory allergens selected from the group of Beta-D-Glucan, dust, molds and endotoxin. Preferably, the donor animals are vaccinated against endotoxin and one or more molds selected from the group of *Aspergillus fumigatus* and *Faenia rectivirgula*. Most preferably, the donor animals are additionally vaccinated against one or more allergens selected from the group of grass, legume, tree, weed pollen, animal dander/epithelia, fungi, mites, insects, and dust.

EXAMPLE 4

Pre-Treatment Diet

A method of producing a blood product, preferably a serum product, in accordance with the present invention includes pre-treating a plurality of donor animals with a diet in a manner to increase blood levels of one or more factors associated with healthy immune response mechanisms. In this example, the diet includes roughage selected from the group of alfalfa, mixed alfalfa/grass, hay and pasture grazing. The diet has a low protein:energy ratio ranging from 72 to 80, preferably 74 to 78, and a reduced soluble carbohydrate source for energy no greater than 14% and preferably ranging from 10.0 to 12.75% of total energy source on a dry matter basis. The diet may also include antioxidant supplements selected from the group of vitamin E, selenium, vitamin A, vitamin C, astaxanthin, and medicinal mushrooms.

In one embodiment, the diet also has a low omega-6:omega-3 ratio between the ranges of 1.5:1 and 10:1 and includes eicosapentaenoic acid (EPA) and docosahexaenoic acid (DHA). The EPA and DHA may be provided by marine fish oils (i.e. Menhaden, sardine, cod, mackerel, and anchovy oil), hill oil or an algal product with an approximate ratio of 1:1.5. The diet is preferably high in total fat with a fat content of at least 4.5%, preferably at least 6%, and most preferably ranging from 6 to 12%.

EXAMPLE 5

Additional Pre-Treatment

A method of producing a blood product, preferably a serum product, in accordance with the present invention includes pre-treating a plurality of donor animals in a manner to increase blood levels of one or more factors associated with healthy immune response mechanisms. In this example, the donor animals are administered at least one treatment selected from the group of oral allergens/antibodies, immunostimulants and antioxidants.

In one embodiment, the donor animals are also administered at least one medicant selected from the group of polysulfated glycosaminoglycans (Adequan), hyaluronic acid (Legend), pentosan phosphate, DMSO, corticosteroids, and resveratrol.

In another embodiment, the donor animals are also administered at least one vitamin or mineral supplement (orally or via injection) selected from the group of vitamin A, vitamin C, vitamin E, selenium, zinc, copper, and mangenese.

In another embodiment, the donor animals also receive oral supplementation of immunomodulating amino acids selected from the group of glutamine, arginine, cysteine, and methionine.

In another embodiment, the donor animals also receive oral supplementation of at least one nutraceutical selected from the group hyaluronic acid, glucosamine, chondroitin, avocado soy unsaponifiables, and methylsulfonylmethane.

In another embodiment, donor animals are also administered a very low-dose of aspirin.

In another embodiment, the donor animals also receive oral administration of at least one herb selected from the group of ginseng, yucca, ginger and similar functioning herbs.

In a preferred embodiment, the donor animals are administered of at least one oral allergen/antibody, at least one immunostimulant, at least one antioxidant, immunomodulating amino acids, at least one oligosaccharide and a low dose of aspirin. In this preferred embodiment, the donor animals may also be administered at least one herb, at least one medicant and at least one probiotic.

EXAMPLE 6

Processing

A method of producing a serum product in accordance with the present invention includes processing the blood in a manner to increase blood levels of one or more factors associated with healthy immune response mechanisms. In this example, the collected blood is kept at ambient room temperature (20-25° C.) for a period of time, preferably 15-60 minutes, followed by transfer to a warm room (30-35° C.) for a period of time, preferably 3-4 hours, and finally transferred to a cool room (2-8° C.) for 24-48 hours of incubation. Alternatively, collected blood could be incubated for 24 hours at 37° C. or another combination of incubation temperature and serum harvest time from 12-48 hours. Clotting stimulants may be added to the collected blood to speed-up the formation, synthesis, and secretion of certain factors In another embodiment, the serum is concentrated to an optimum concentration and viscosity for the route of administration anticipated to the patient animal to allow efficient administration of the dosage necessary to reduce inflammation. Preferably, the serum is concentrated by a factor of 1.5-5×, more preferably 2-4×, and most preferably 4×.

EXAMPLE 7

Collected Blood

A method of producing a blood product, preferably a serum product, in accordance with the present invention includes pre-treating a plurality of donor animals in a manner such that the blood collected from the donor animals after pre-treatment has increased total fatty acids, increased polyunsaturated fatty acids, increased omega-3 and omega-6 fatty acids, a decreased omega-6:omega-3 ratio, increased α-linolenic acid, increased docosahexaenoic acid and increased eicosapentaenoic acid over that of the blood of the donor animals prior to the pre-treatment and/or over that of the blood collected from the control group of Example 1.

In one embodiment, the collected blood also has increased total white blood cells (including increased neutrophils and monocytes with increases or decreases in lymphocytes and eosinophils), increased neutrophils and increased monocytes over that of the blood of the donor animals prior to the pre-treatment and/or over that of the blood collected from the control group of Example 1. The collected blood may also have increased platelets.

In another embodiment, the collected blood also has increased total protein, decreased albumin, increased globulin, and a decreased albumin/globulin ratio over that of the blood of the donor animals prior to the pre-treatment and/or over that of the blood collected from the control group of Example 1.

In another embodiment, the collected blood also has decreased creatine phosphokinase, increased iron, and increased total iron binding capacity over that of the blood of the donor animals prior to the pre-treatment and/or over that of the blood collected from the control group of Example 1. In addition, the collected blood may have increased fibrinogen.

In another embodiment, the collected blood also has decreased concentration triglycerides, increased cholesterol, and improved glucose levels, decreased blood urea nitrogen (BUN) and decreased BUN/Creatin ratio over that of the blood of the donor animals prior to the pre-treatment and/or over that of the blood collected from the control group of Example 1.

The increases and decreases in the blood components are sufficient to collectively result in an enhanced profile, wherein the overall component concentrations in the blood is sufficient to enhance or improve the therapeutic effectiveness of the blood product in preventing or mitigating immune conditions or diseases.

EXAMPLE 8

Serum Product

A method of producing a serum product in accordance with the present invention includes pre-treating a plurality of donor animals in a manner such that the serum produced from blood collected from the donor animals after pre-treatment has increased docosahexaenoic acid (DHA) and increased eicosapentaenoic acid (EPA) over that of the blood of the donor animals prior to the pre-treatment and/or over that of the blood collected from the control group of Example 1. The collected blood before serum harvest may also have increased platelets.

In one embodiment, the serum also has increased immunoglobulins and subtypes to neutralize allergen and pathogen antigens over that of the blood of the donor animals prior to the pre-treatment and/or over that of the blood collected from the control group of Example 1.

In another embodiment, the serum also has increased resolution mediators selected from the group of resolvins, protectins, lipoxins, and maresins over that of the blood of the donor animals prior to the pre-treatment and/or over that of the blood collected from the control group of Example 1.

In another embodiment, the serum also has decreased pro-inflammatory cytokines selected from the group of IL-1β and TNF-α and increased anti-inflammatory cytokines selected from the group of IL-10, IL-1RA over that of the blood of the donor animals prior to the pre-treatment and/or over that of the blood collected from the control group of Example 1.

In another embodiment, the serum also has optimal levels of healing growth factors selected from the group consisting of TGF-β, PDGF, VEGF, IGF, and EGF over that of the blood of the donor animals prior to the pre-treatment and/or over that of the blood collected from the control group of Example 1.

In another embodiment, the serum also has an increase in less inflammatory eicosanoids (i.e. 3 and 5 series) while still maintaining constitutive production of necessary prostaglandins (i.e. PGE2) over that of the blood of the donor animals prior to the pre-treatment and/or over that of the blood collected from the control group of Example 1.

In another embodiment, the serum also has increased antioxidant levels over that of the blood of the donor animals prior to the pre-treatment and/or over that of the blood collected from the control group of Example 1.

In another embodiment, the serum also has increased anti-inflammatory microRNAs.

In another embodiment, the serum also exhibits conversion of immune response factors from pro-inflammatory to pro-resolution wherein the neutrophils and macrophages in the collected blood had to undergo a phenotype switch in comparison to the blood of the donor animals prior to the pre-treatment and/or over that of the blood collected from the control group of Example 1.

In another embodiment, the serum also has increased anti-cytokine antibodies that neutralize pro-inflammatory cytokines selected from the group of neutralizing antibodies for TNF-α and IL-1 over that of the blood of the donor animals prior to the pre-treatment and/or over that of the blood collected from the control group of Example 1.

In another embodiment, the serum also has increased soluble cytokine receptors selected from the group TNF-α, IL-6, IL-1β, IL-8, and IL-18 over that of the blood of the donor animals prior to the pre-treatment and/or over that of the blood collected from the control group of Example 1.

In another embodiment, the serum also has increased Annexin-1A (Lipocortin) over that of the blood of the donor animals prior to the pre-treatment and/or over that of the blood collected from the control group of Example 1.

In another embodiment, the serum also has increased TIMPs over that of the blood of the donor animals prior to the pre-treatment and/or over that of the blood collected from the control group of Example 1.

In another embodiment, the serum also has increased surfactant proteins a and increased Clara Cell Secretory Protein over that of the blood of the donor animals prior to the pre-treatment and/or over that of the blood collected from the control group of Example 1.

In another embodiment, the serum also has an increased concentration of altered lymphokines over that of the blood of the donor animals prior to the pre-treatment and/or over that of the blood collected from the control group of Example 1.

In another embodiment, the serum also has increased complement components selected from the group C3, C3a and C3b. In another embodiment, the serum also has increased panprotease inhibitors selected from the group alpha-2 macroglobulin and alpha-1 antitrypsin.

In another embodiment, the serum also has increased constituents influencing T reg cells, impacting Th1, Th2, and Th17 response pathways, diminishing NF-KB activity, and diminishing TLR response pathways.

The increases and decreases in the serum components are sufficient to collectively result in an enhanced profile, wherein the overall component concentrations in the blood is sufficient to enhance or improve the therapeutic effectiveness of the serum in preventing or mitigating immune conditions or diseases.

EXAMPLE 9

Exemplary Pre-Treatment for Enhanced Profile

A method of producing a blood product, preferably a serum product, in accordance with the present invention includes pre-treating a plurality of donor animals as follows:
 a. vaccinating the donor animals against one or more bacterial antigens, one or more viral antigens and one or more allergens;
 b. feeding the donor animals a diet with a low protein: energy ratio ranging from 72 to 80, preferably 74 to 78 on a dry matter basis;
 c. feeding the donor animals a diet with a fat content of at least 4.5%, preferably at least 6%, and more preferably 10-12%;
 d. administering at least one additional treatment to the donor animals selected from the group of oral allergens/antibodies, immunostimulants and antioxidants.

Preferably the diet has a low omega-6:omega-3 ratio between the ranges of 1.5:1 and 10:1.

In this example, the pre-treatment regimen is preferably consistently implemented with respect to the members of the donor group to ensure that the blood levels of the desired anti-inflammatory profile components are sufficiently high. Preferably, the donors are pre-treated for at least thirty days, more preferably, the donors are pre-treated for a period of one to three months, and most preferably, and the donors are pre-treated for at least 90 days. After the donors are pre-treated for the prescribed period of time, blood can be collected having an enhanced profile over that of the blood of the donor animals prior to pre-treatment.

EXAMPLE 10

Exemplary Pre-Treatment for Enhanced Equine Blood Profile

A method of producing an equine blood product, preferably a serum product, in accordance with the present invention includes pre-treating a plurality of donor horses as follows:
 a. vaccinating the donor horses against one or more bacterial antigens known to be equine respiratory pathogens;
 b. vaccinating the donor horses against one or more viral antigens known to be equine respiratory pathogens;
 c. vaccinating the donor horses against one or more equine respiratory allergens;
 d. feeding the donor horses a diet with a fat content of at least 4.5% and having a low omega-6:omega-3 ratio between the ranges of 1.5:1 and 10:1, preferably, the diet includes eicosapentaenoic acid (EPA) and docosahexaenoic acid (DHA).
 e. administering at least one oral allergen/antibody, immunostimulant, antioxidant, immunomodulating amino acids, at least one oligosaccharide and a low dose of aspirin.

Preferably, the donor horses are vaccinated against endotoxin and one or more molds selected from the group of *Aspergillus fumigatus* and *Faenia rectivirgula*. The donor animals may additionally be vaccinated against the bacterial antigens selected from the group consisting of *Streptococcus equi* and *Rhodococcus equi* and against the viral antigens selected from the group Equine Herpes Virus (EHV; 1,2,4,5) and Equine Influenza Virus (EIV);

In a preferred embodiment, the donor animals are also administered at least one herb, at least one medicant and at least one probiotic.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims. This reference would include the discovery of new proteins in serum/blood used to manipulate the immune system and any exogenous means of manipulating these components.

What is claimed and desired to be secured by Letters Patent is as follows:

1. A treatment method for treating and/or mitigating a respiratory condition in an equine patient, said method comprising administrating a blood product to the equine patient via localized delivery to the lungs, wherein said blood product is produced via a method of production comprising the following steps:
   a. pre-treating at least one donor horse with a diet and immunization regimen for at least one month comprising:
      i. feeding said donor horse a combined amount of EPA and DHA of at least 4.25 mg/kg body weight of the donor horse per day with the EPA:DHA ratio ranging from 1:5-5:1, and alfalfa hay; and
      ii. immunizing said donor horse with Rhodococcus equi.;
   b. collecting blood from said at least one donor horse; and
   c. processing said collected blood to produce said blood product.

2. The treatment method of claim 1 wherein the respiratory condition is selected from the group consisting of Exercise-Induced Pulmonary Hemorrhage (EIPH), Inflammatory Airway Disease (IAD), Recurrent Airway Obstruction (RAO) and Chronic Obstructive Pulmonary Disease (COPD).

3. The treatment method of claim 1 wherein the blood product is administered via intranasal administration, transnasal catheter administration, intratracheal administration, intrabronchial spray administration, and/or nebulization administration.

4. The treatment method of claim 3, wherein the blood product is administered via nebulization administration.

5. The treatment method of claim 4, wherein the blood product is encapsulated in microspheres.

6. The treatment method of claim 1 wherein the blood product is administered in a dose amount of 1 mL to 80 mL of a 0.12 gm IgG/mL blood product.

7. The treatment method of claim 6 wherein the blood product is administered in said dose amount for an initial dosing of five times, 24 hours apart.

8. The treatment method of claim 7, wherein the blood product is additionally administered in said dose amount once a week after the initial dosing.

9. The treatment method of claim 6, wherein the blood product is administered in said dose amount 24-48 hours prior to a competition, strenuous exercise and/or long-distance transport.

10. The treatment method of claim 1, wherein said pre-treating comprises feeding said donor horse said combined amount of EPA and DHA consisting of fish oil.

11. The treatment method of claim 1, wherein said pre-treating comprises feeding said donor horse said combined amount of EPA and DHA consisting of fish oil and tuna oil.

12. The treatment method of claim 1, wherein said pre-treating additionally comprises immunizing said donor horse with the following additional vaccinations *Streptococcus equi, Escherichia coli,* 7-way Clostridial, equine herpes virus and equine influenza.

13. The treatment method of claim 12, wherein said pre-treating additionally comprises immunizing said donor animal with one or more respiratory allergens selected from the group consisting of *Aspergillus fumigatus, Faenia rectivirgula,* endotoxin, Beta-D-Glucan, dust, animal dander/epithelia, fungi and mites.

14. A treatment method for treating an equine patient for a respiratory condition selected from the group consisting of Exercise-Induced Pulmonary Hemorrhage (EIPH), Inflammatory Airway Disease (IAD), Recurrent Airway Obstruction (RAO), and Chronic Obstructive Pulmonary Disease (COPD), said treatment method comprising administering a blood product to the equine patient via intranasal administration, transnasal catheter administration, intratracheal administration, intrabronchial spray administration, and/or nebulization administration, wherein the blood product is produced by a production method comprising the following steps:
   a. selecting two or more donor horses, wherein said donor horses are mature, and originate from at least two geographic locations, wherein said geographic locations are at least 100 miles apart;
   b. pre-treating said two or more donor horses with a diet and an immunization regimen for at least a month comprising;
      i. feeding said donor horse a combined amount of EPA and DHA ranging from 60 mg/kg body weight of the donor horse per day to 65 mg/kg body weight of the donor horse per day with the EPA:DHA ratio ranging from 1:5-5:1, and alfalfa hay; and
      ii. immunizing said donor horse with the following vaccinations:
   *Rhodococcus equi, Streptococcus equi, Escherichia coli,* 7-way Clostridial, equine herpes virus and equine influenza;
   c. collecting blood from said two or more donor animals; and
   d. processing said blood into a blood product.

15. The method of claim 14, wherein the respiratory condition is selected from the group consisting of Recurrent Airway Obstruction (RAO) and Chronic Obstructive Pulmonary Disease (COPD).

16. The method of claim 14, wherein said administering step comprises nebulization administration.

17. The method of claim 14, wherein said feeding step comprises feeding said donor horse a combined amount of EPA and DHA sourced from fish oil.

18. The method of claim 14, wherein said blood product is administered in a dose amount of 1 mL to 80 mL of a 0.12 gm IgG/mL blood product.

* * * * *

UNITED STATES PATENT AND TRADEMARK OFFICE
CERTIFICATE OF CORRECTION

PATENT NO. : 11,419,893 B2
APPLICATION NO. : 16/902560
DATED : August 23, 2022
INVENTOR(S) : Tammi Sue Epp et al.

It is certified that error appears in the above-identified patent and that said Letters Patent is hereby corrected as shown below:

In the Specification

Column 9, Line 7, delete "hill" and replace it with -- krill --.

Column 9, Line 16, delete "musculo skeletal" and replace it with -- musculoskeletal --.

Column 34, Line 3, delete "micro spheres" and replace it with -- microspheres --.

Column 36, Line 41, delete "hill" and replace it with -- krill --.

Signed and Sealed this
Eleventh Day of October, 2022

Katherine Kelly Vidal
*Director of the United States Patent and Trademark Office*